(12) United States Patent
Wada et al.

(10) Patent No.: US 7,918,961 B2
(45) Date of Patent: Apr. 5, 2011

(54) WORN ARTICLE AND METHOD FOR PRODUCING THE SAME

(75) Inventors: Takao Wada, Osaka (JP); Masaki Nakakado, Osaka (JP)

(73) Assignee: Zuiko Corporation, Osaka (JP)

( * ) Notice: Subject to any disclaimer, the term of this patent is extended or adjusted under 35 U.S.C. 154(b) by 888 days.

(21) Appl. No.: 10/598,028

(22) PCT Filed: Feb. 7, 2005

(86) PCT No.: PCT/JP2005/001774
§ 371 (c)(1),
(2), (4) Date: Aug. 16, 2006

(87) PCT Pub. No.: WO2005/079720
PCT Pub. Date: Sep. 1, 2005

(65) Prior Publication Data
US 2007/0142808 A1 Jun. 21, 2007

(30) Foreign Application Priority Data

Feb. 23, 2004 (JP) ................................ 2004-046149
Jun. 11, 2004 (JP) ................................ 2004-174047

(51) Int. Cl.
*B32B 37/00* (2006.01)
*B32B 37/02* (2006.01)
*B32B 38/00* (2006.01)
*B32B 38/04* (2006.01)

(52) U.S. Cl. ........ 156/259; 156/250; 156/252; 156/253; 156/256; 156/269; 156/270; 156/271; 604/385.01; 604/385.3; 604/385.22

(58) Field of Classification Search .................. 156/250, 156/252–254, 256, 259, 269–271, 169–171; 604/385.3, 385.22, 385.1, 385.01
See application file for complete search history.

(56) References Cited

U.S. PATENT DOCUMENTS
5,224,405 A * 7/1993 Pohjola ............................ 83/24
(Continued)

FOREIGN PATENT DOCUMENTS
EP 1 308 147 A2 5/2003
(Continued)

OTHER PUBLICATIONS
International Search Report for corresponding Application No. PCT/JP2005/001774 mailed Mar. 15, 2005.

*Primary Examiner* — Mark A Osele
*Assistant Examiner* — Christopher C Caillouet
(74) *Attorney, Agent, or Firm* — Renner, Otto, Boisselle & Sklar, LLP

(57) ABSTRACT

The present invention relates to a new worn article, which gives a close fit and with which it is possible to reduce the production cost. A worn article of the present invention includes a main body portion 20 including an absorbent core 25 and covering a front torso area, a crotch area and a rear torso area of a wearer, and a pair of side panels PL and PR attached to the main body portion 20 and located between the front and rear torso areas when the worn article is worn. Each of the side panels PL and PR is stretchable in an around-the-torso direction X. At least a portion of the side panel PL and PR includes an elastic thread G sandwiched between at least two sheet-like materials S1 and S2 and is in a contracted state where the elastic thread is contracted, thus forming gathers.

8 Claims, 23 Drawing Sheets

U.S. PATENT DOCUMENTS

| | | | | |
|---|---|---|---|---|
| 5,226,992 A * | 7/1993 | Morman | 156/62.4 |
| 5,399,219 A * | 3/1995 | Roessler et al. | 156/259 |
| 5,595,618 A * | 1/1997 | Fries et al. | 156/164 |
| 5,705,013 A * | 1/1998 | Nease et al. | 156/260 |
| 6,086,571 A * | 7/2000 | Guevara et al. | 604/385.29 |
| 6,174,303 B1 * | 1/2001 | Suprise et al. | 604/385.29 |
| 6,197,012 B1 | 3/2001 | Mishima et al. | |
| 6,645,190 B1 * | 11/2003 | Olson et al. | 604/389 |
| 6,667,085 B1 * | 12/2003 | McNichols | 428/40.1 |
| 6,748,996 B2 * | 6/2004 | Nakakado et al. | 156/556 |
| 2002/0002358 A1 * | 1/2002 | Durrance et al. | 604/385.01 |
| 2002/0103468 A1 | 8/2002 | Nakakado et al. | |
| 2004/0035521 A1 * | 2/2004 | Nakakado et al. | 156/229 |
| 2004/0123938 A1 * | 7/2004 | Neculescu et al. | 156/160 |
| 2004/0238105 A1 * | 12/2004 | Schneider et al. | 156/179 |

FOREIGN PATENT DOCUMENTS

| | | |
|---|---|---|
| JP | 63-317576 | 12/1988 |
| JP | 04-261655 | 9/1992 |
| JP | 07-080023 | 3/1995 |
| JP | 07-051143 | 6/1995 |
| JP | 07-252762 | 10/1995 |
| JP | 10-286279 | 10/1998 |
| JP | 2000-500684 | 1/2000 |
| JP | 2000-510349 | 8/2000 |
| JP | 2002-345889 | 12/2002 |
| JP | 2003-199790 | 7/2003 |
| WO | 95/19258 | 7/1995 |
| WO | 96/03952 | 2/1996 |
| WO | 97/47265 | 12/1997 |

* cited by examiner

FIG. 4
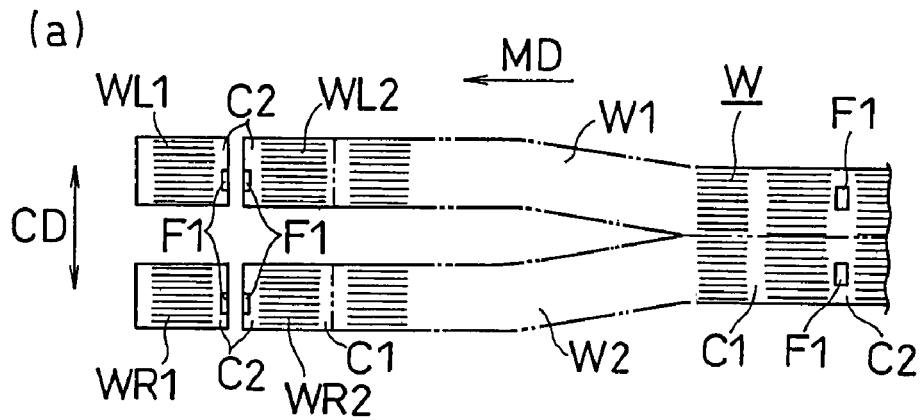
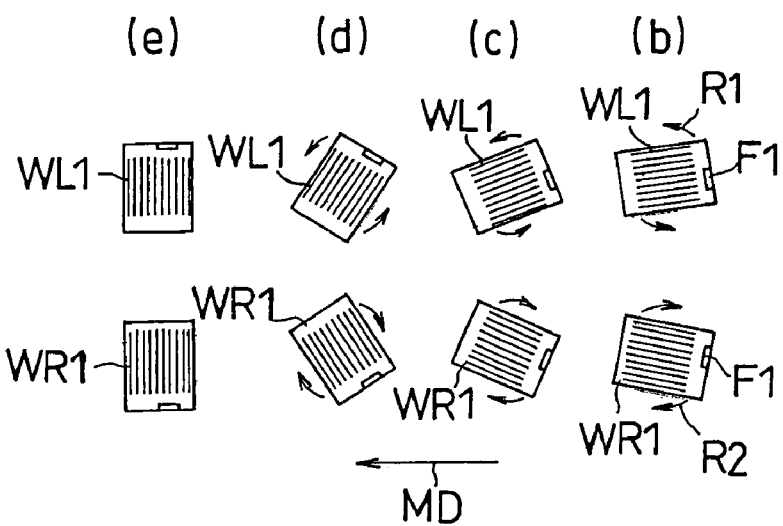
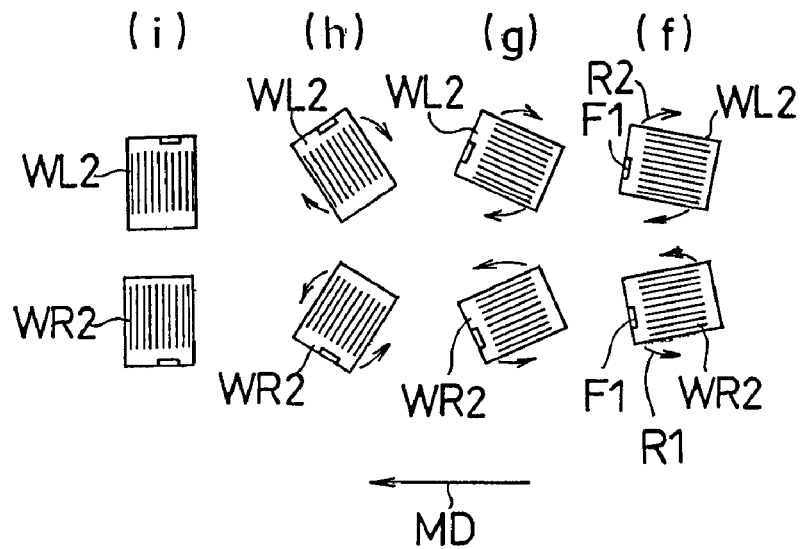

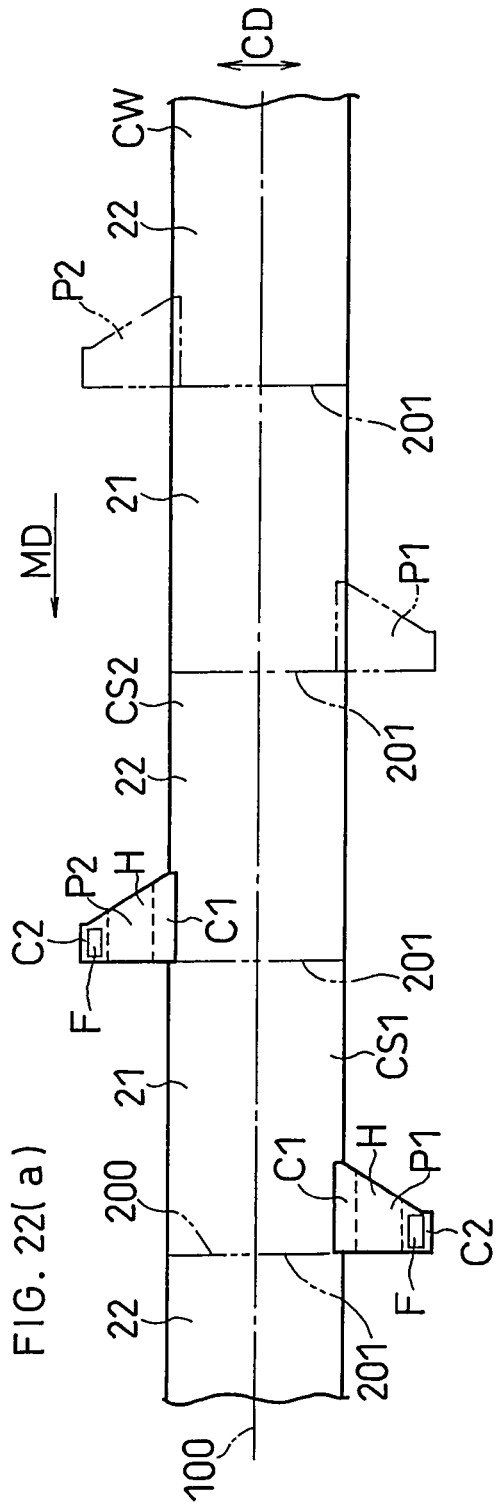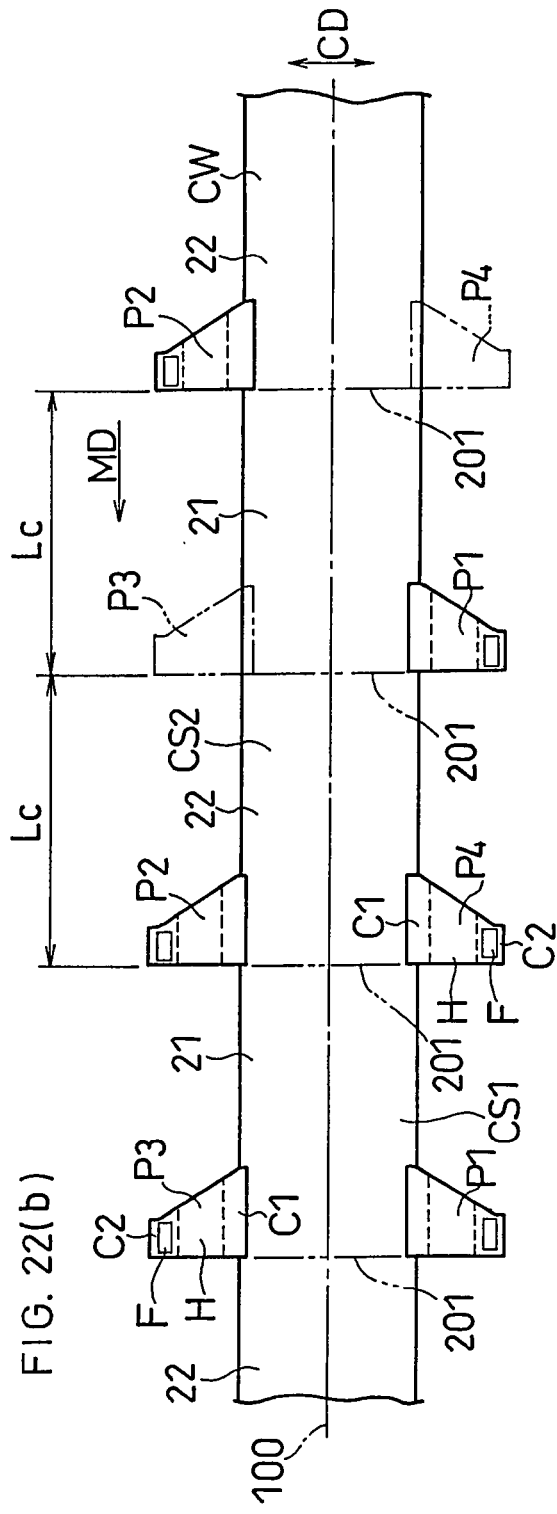

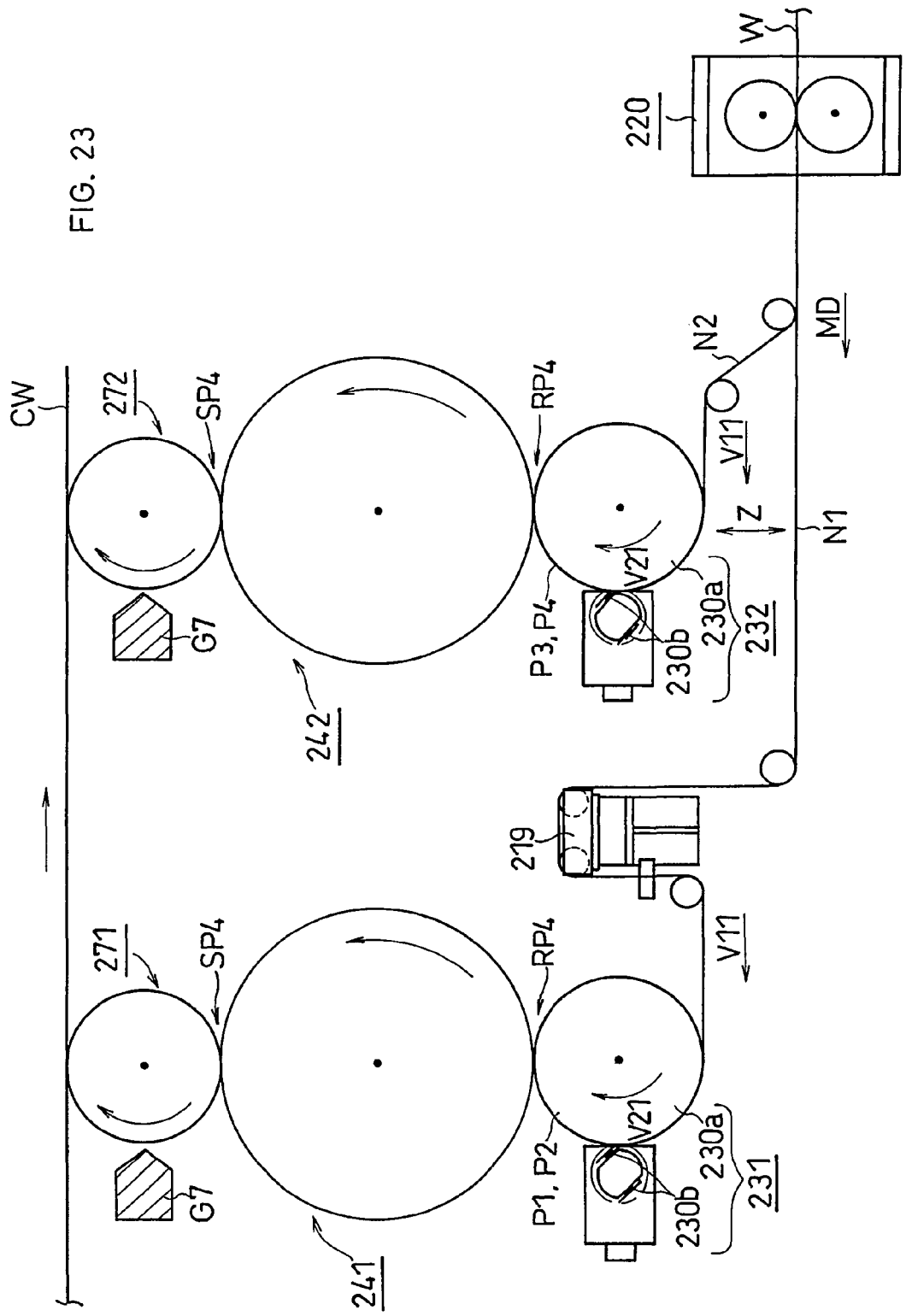

WORN ARTICLE AND METHOD FOR PRODUCING THE SAME

TECHNICAL FIELD

The present invention relates to a worn article and a method for producing the same.

BACKGROUND ART

The first to fourth patent documents, identified below, disclose worn articles, such as disposable diapers and underpants, that are stretchable in the around-the-torso direction, and methods for producing the same.

[First Patent Document] Japanese Laid-Open Patent Publication No. 10-286279

[Second Patent Document] Japanese Laid-Open Patent Publication No. 7-80023

[Third Patent Document] Japanese National Phase PCT Laid-Open Publication No. 2000-500684 (WO97/47265)

[Fourth Patent Document] Japanese National Phase PCT Laid-Open Publication No. 2000-510349 (WO96/03952)

The first patent document discloses a worn article having a stretchable side panel, which includes an extensible sheet and an elastically stretchable hot-melt adhesive.

The second patent document discloses a method for producing a worn article having a side panel formed with a material that is extensible in the direction (the CD direction) perpendicular to the flow direction of the sheet.

The third patent document discloses a method for producing a worn article having a side panel formed by cutting a material extensible in multi-directions in a non-wasteful manner.

The fourth patent document discloses a method for producing a worn article having a side panel formed with a material stretchable in the CD direction.

DISCLOSURE OF THE INVENTION

However, extensible sheets are expensive and the side panel is formed by using an extensible sheet in the first patent document, whereby the production cost of the worn article will be high.

Since the stretch of an extensible sheet is smaller than that of an elastic thread, it is not possible to obtain a sufficiently desirable fit.

Therefore, an object of the present invention is to provide a new worn article, which gives a close fit and with which it is possible to reduce the production cost.

In the second to fourth patent documents, a side panel using a material extensible in the direction (the CD direction) perpendicular to the flow direction of the sheet is fastened to the absorbent main body portion. When producing a side panel in which the elastic thread is sandwiched between sheets, a material is used that is stretchable in the flow direction of the sheet (the MD direction). However, the patent documents fail to disclose a production method that uses a material stretchable in the flow direction.

Another object of the present invention is to provide a new method with which it is possible to produce a worn article having such side panels.

A worn article of the present invention includes a main body portion including an absorbent core and covering a front torso area, a crotch area and a rear torso area of a wearer, and a pair of side panels attached (fixed) to the main body portion and located between the front and rear torso areas when the worn article is worn, wherein each of the side panels is stretchable in an around-the-torso direction (a direction along a periphery of the torso (waist) of a wearer). At least a portion of the side panel includes an elastic thread sandwiched between at least two sheet-like materials and is in a contracted state where the elastic thread is contracted, thus forming gathers (shirring).

In this worn article, the elastic thread between the at least two sheet-like materials is shrunk to form gathers in the side panels, and the side panels thereby exhibit substantial stretchability. Therefore, the fit is improved.

Since the side panel is formed by sandwiching an elastic thread between a pair of sheet-like materials, it is possible to reduce the production cost as compared with a case where expensive extensible sheets are used, such as elastic films or extensible non-woven fabric sheets.

In a preferred embodiment of the worn article of the present invention, a first non-contractile portion where a contractile force from the elastic thread is not active is provided in a portion of the side panel that is joined to the main body portion, and the first non-contractile portion is laid over and attached to the main body portion.

In a case where such a first non-contractile portion is provided, the first non-contractile portion is not contracted (shrunk) by the contractile force from the elastic thread. Therefore, the flat first non-contractile portion where no gathers are formed can be laid over and joined to the main body portion, thereby facilitating the attachment of the side panels to the main body portion.

In a further preferred embodiment of the worn article of the present invention, a second non-contractile portion where a contractile force from the elastic thread is not active is provided in a tip portion of the side panel in the around-the-torso direction. A fastening element is attached to the second non-contractile portion, the fastening element being used for fastening the side panels to the main body portion when the worn article is worn.

In a case where such a second non-contractile portion is provided, the second non-contractile portion is not contracted by the contractile force from the elastic thread. Therefore, the fastening element can be placed while being laid over the flat second non-contractile portion where no gathers are formed, thereby facilitating the attachment of the fastening element to the side panels.

A production method for obtaining the worn article of the present invention is a method for producing a worn article in which a pair of side panels each including two sheet-like materials and an elastic member sandwiched between the two sheet-like materials are attached to a main body portion. The production method includes the steps of: feeding an elastic member between a pair of sheet-like materials along a flow direction of the pair of sheet-like materials so as to obtain a laminate to be the side panels; cutting off the laminate at a predetermined interval in the flow direction to obtain cut panels; changing an attitude of a pair of cut panels including two of the cut panels adjacent to each other to an attitude that is obtained by a rotation of about 90 degrees with respect to the flow direction (i.e., the attitude of the pair of cut panels are changed by rotating the pair of cut panels about a normal line perpendicular to the plane of the cut panels so that the longitudinal direction (the stretching direction) of each cut panel is orthogonal to the flow direction); spacing the pair of cut panels apart from each other; and attaching the pair of cut panels to a sheet-like member to be the main body portion, one on a left side and the other on a right side of the sheet-like materials.

In the present invention, the term "a sheet-like member to be the main body portion" means a member to be the main body portion in a produced worn article, and may be either an uncut member being continuous in the flow direction of the sheet-like member or a member that has been cut in a shape of the main body portion.

Another production method for obtaining the worn article of the present invention is a method for producing a worn article in which a pair of side panels each including two sheet-like materials and an elastic member sandwiched between the two sheet-like materials are attached to a main body portion. The production method includes the steps of: feeding an elastic member between a pair of sheet-like materials along a flow direction of the pair of sheet-like materials so as to obtain a laminate to be the side panels; cutting the laminate along a cut-off line (cutting line) extending in the flow direction to produce first and second divided laminates, which are separated from each other in a width direction of the sheet-like materials; cutting each of the first and second divided laminates at a predetermined interval in the flow direction to obtain a left cut panel and a right cut panel; spacing the first and second divided laminates apart from each other in the width direction or spacing the left and right cut panels apart from each other in the width direction; changing an attitude of each cut panel to an attitude that is obtained by a rotation of about 90 degrees with respect to the flow direction (i.e., the attitude of each cut panel is changed by rotating each cut panel about a normal line perpendicular to the plane of the cut panel so that the longitudinal direction (the stretching direction) of each cut panel is orthogonal to the flow direction); and attaching the left cut panel and the right cut panel, whose attitudes have been changed, on a left side and a right side, respectively, of a sheet-like member to be the main body portion.

Still another production method for obtaining the worn article of the present invention is a method for producing a worn article in which a pair of side panels each including two sheet-like materials and an elastic member sandwiched between the two sheet-like materials are attached to a main body portion. The production method includes the steps of: feeding an elastic member between a pair of sheet-like materials along a flow direction of the pair of sheet-like materials so as to obtain a laminate to be the side panels; cutting the laminate along a predetermined wave-shaped cut-off line extending in the flow direction to produce first and second divided laminates, which are separated from each other in a width direction of the sheet-like materials; cutting the first divided laminate at a predetermined interval in the flow direction to obtain first cut panels; changing an attitude of a pair of first cut panels including two of the first cut panels adjacent to each other to an attitude that is obtained by a rotation of about 90 degrees with respect to the flow direction; attaching the pair of first cut panels whose attitude has been changed to a sheet-like member to be the main body portion, one on a left side and the other on a right side of the sheet-like member; cutting the second divided laminate at a predetermined interval in the flow direction to obtain second cut panels; changing an attitude of a pair of second cut panels including two of the second cut panels adjacent to each other to an attitude that is obtained by a rotation of about 90 degrees with respect to the flow direction; and attaching the pair of second cut panels whose attitude has been changed to the sheet-like member to be the main body portion, one on the left side and the other on the right side of the sheet-like member.

The production method may include a step of spacing a pair of first cut panels apart from each other and/or a step of spacing a pair of second cut panels apart from each other.

In the present invention, it is preferred that the cut panels are formed without being trimmed. However, the cut panels may be formed by being trimmed.

The term "trimming" means cutting away an unnecessary portion of a member for the purpose of improving the fitting property or the aesthetic quality of the product. The terms "trim", "trim waste", "loss" and "lost portion" refer to a portion to be removed or a portion that has been removed in the trimming process.

The production method of the present invention may further include a step of attaching a fastening element to the laminate, the fastening element being used for fastening the side panels to the main body portion when the worn article is worn, wherein in the step of cutting the laminate to obtain the cut panels, the fastening element, together with the laminate, is cut into two pieces so that one cut-off fastening element is provided for each cut panel. In other words, a fastening element may be attached to the laminate, and the laminate is cut so that the fastening element is divided into two pieces. Thus, a small fastening element can easily be attached to the cut panel.

The fastening element does not have to be cut when the laminate is cut, or the fastening element may be attached to the cut panel after the laminate is cut.

In a production method of the present invention, non-contractile portions where a contractile force from the elastic member is not active may be formed in the laminate at a predetermined interval in the flow direction, and, in the step of cutting the laminate to obtain the cut panels, the laminate may be cut along each non-contractile portion so that the non-contractile portion is provided for each cut panel.

Thus, the non-contractile portions are formed in the laminate, and the laminate is cut along each non-contractile portion to obtain the cut panel, whereby it is possible to easily form the above-mentioned first and second non-contractile portions.

The non-contractile portion may be formed by cutting elastic threads with a cutter, or the like, into short pieces at both end portions of the cut panel, after obtaining the cut panel.

In the present invention, in the step of feeding the elastic material to obtain the laminate to be the side panels, the elastic member may be fed between the pair of sheet-like materials while the elastic member is being extended in the flow direction to produce the laminate, and then the elastic member of the laminate or the cut panels may be relaxed (slackened) so as to form gathers in the laminate or the cut panels.

Thus, it is possible to obtain a side panel having gathers by sandwiching the elastic member being in an extended state between the sheet-like materials and then relaxing the elastic member in the laminate or the cut panel.

The step of relaxing the elastic member may be performed after obtaining the laminate and before attaching the cut panels to the sheet-like member to be the main body portion. In order to facilitate the production of such a side panel, it is typically preferred to relax the elastic member before the step of cutting the laminate to obtain cut panels.

In the present invention, the elastic thread used as the elastic member may be a polyurethane-based elastic thread, a polystyrene-based elastic thread or a natural rubber-based elastic thread. It is preferred that elastic threads are arranged with a density of three threads per inch or higher in order to realize an appropriate fit. It is preferred that the stress to be caused on the side panel when the side panel is pulled is set to be 0.3 kgf per inch or more.

BRIEF DESCRIPTION OF THE DRAWINGS

FIG. 4 is a process diagram showing a production process of a modified embodiment.

FIGS. 22(a) and 22(b) are schematic plan views showing positions where cut panels of the fourth embodiment are fastened to the main body portion.

FIG. 23 shows a schematic side-view layout of a production apparatus of the fourth embodiment.

DESCRIPTION OF THE REFERENCE NUMERALS

25: Absorbent core
20: Absorbent main body portion
C1: First non-contractile portion
C2: Second non-contractile portion
CD: Width direction
F1: First touch fastener (fastening element)
G: Elastic thread (elastic member)
MD: Flow direction
N1: First divided laminate
N2: Second divided laminate
PL, PR: Side panel
S1: First sheet-like material S2: Second sheet-like material
W: Laminate
W1: First laminate
W2: Second laminate
WL1, WR1, P1: First cut panel
WL2, WR2, P2: Second cut panel
P3: Third cut panel
P4: Fourth cut panel

BEST MODE FOR CARRYING OUT THE INVENTION

Embodiments of the present invention will now be described with reference to the drawings.

First, before describing a production method of the present invention, an example of a worn article that can be produced by the production method will be described.

First Embodiment

Worn Article

Figure 1A:
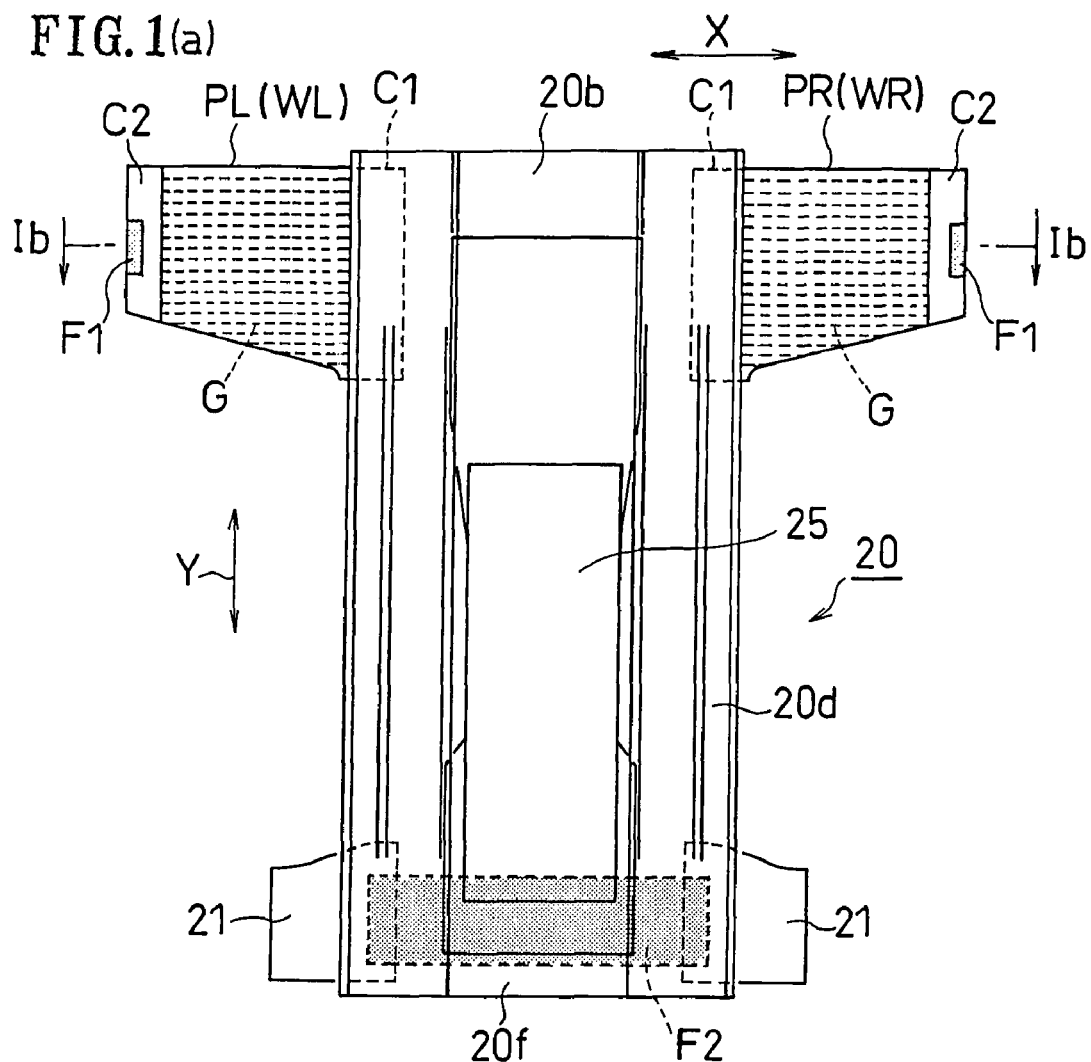
FIG. 1(a) is a schematic plan view showing a worn article in an extended state according to the first embodiment of the present invention.
Figure 1B:
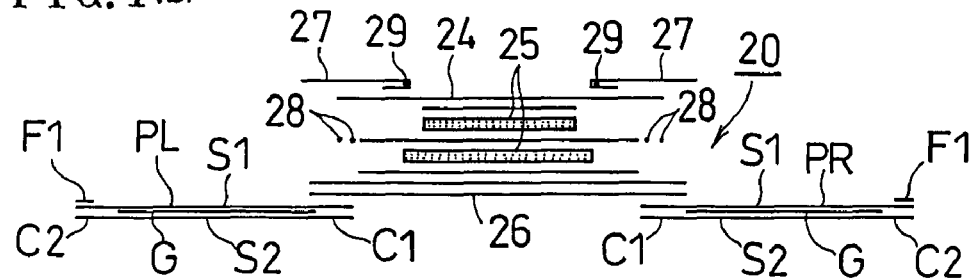
FIG. 1(b) is a cross-sectional view taken along line Ib-Ib.
Figure 1C:
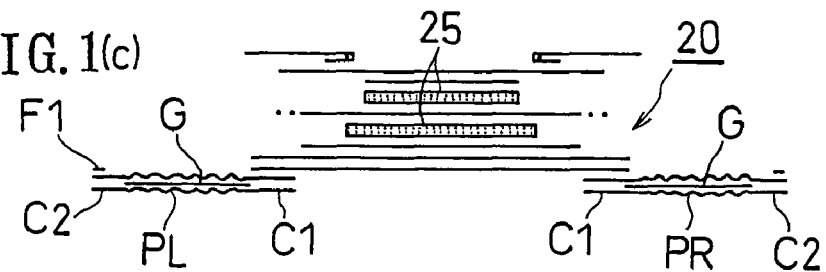
FIG. 1(c) is a cross-sectional view taken along the same line showing a contracted state.
Figure 2:
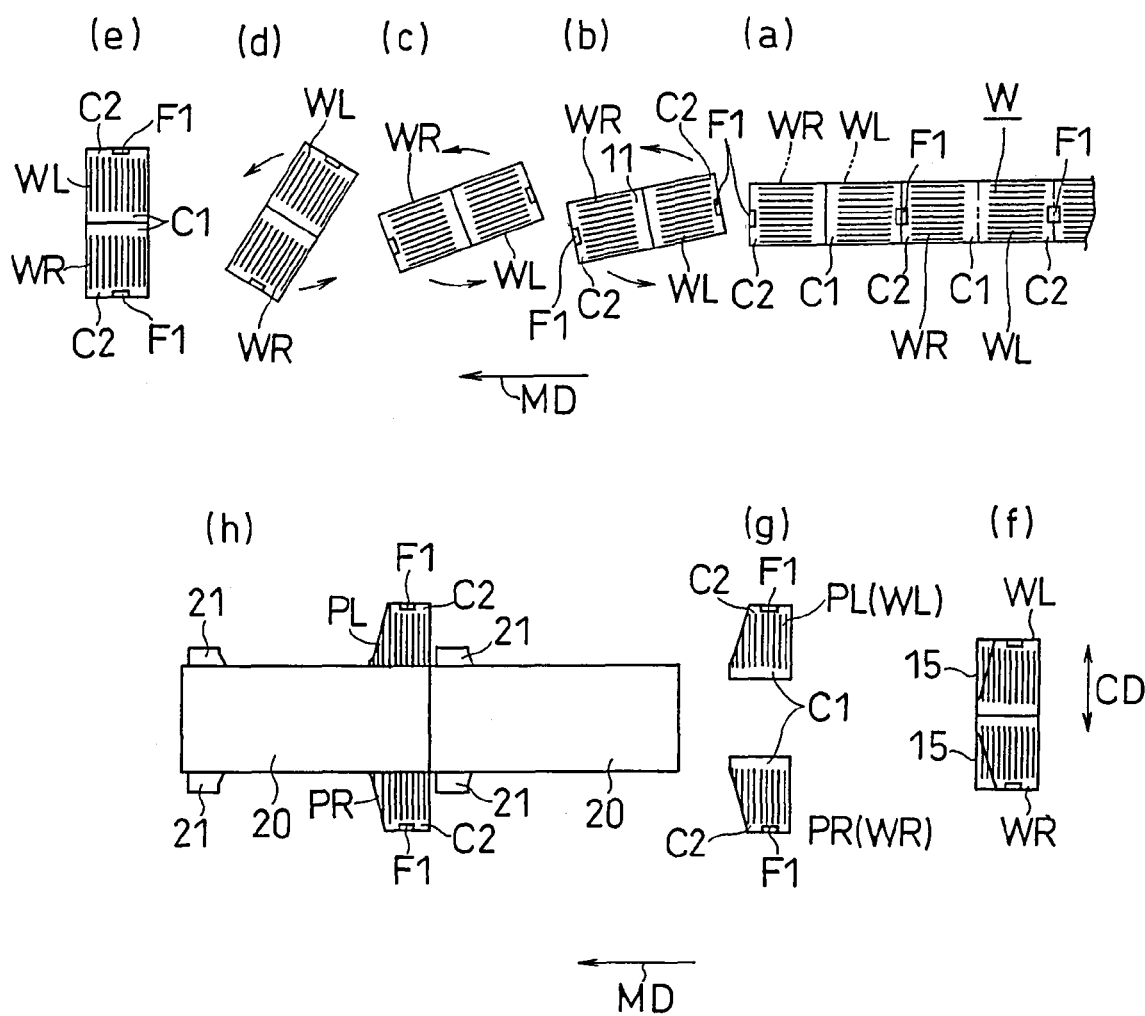
FIG. 2 is a process diagram showing a production process of the first embodiment.
Figure 3:
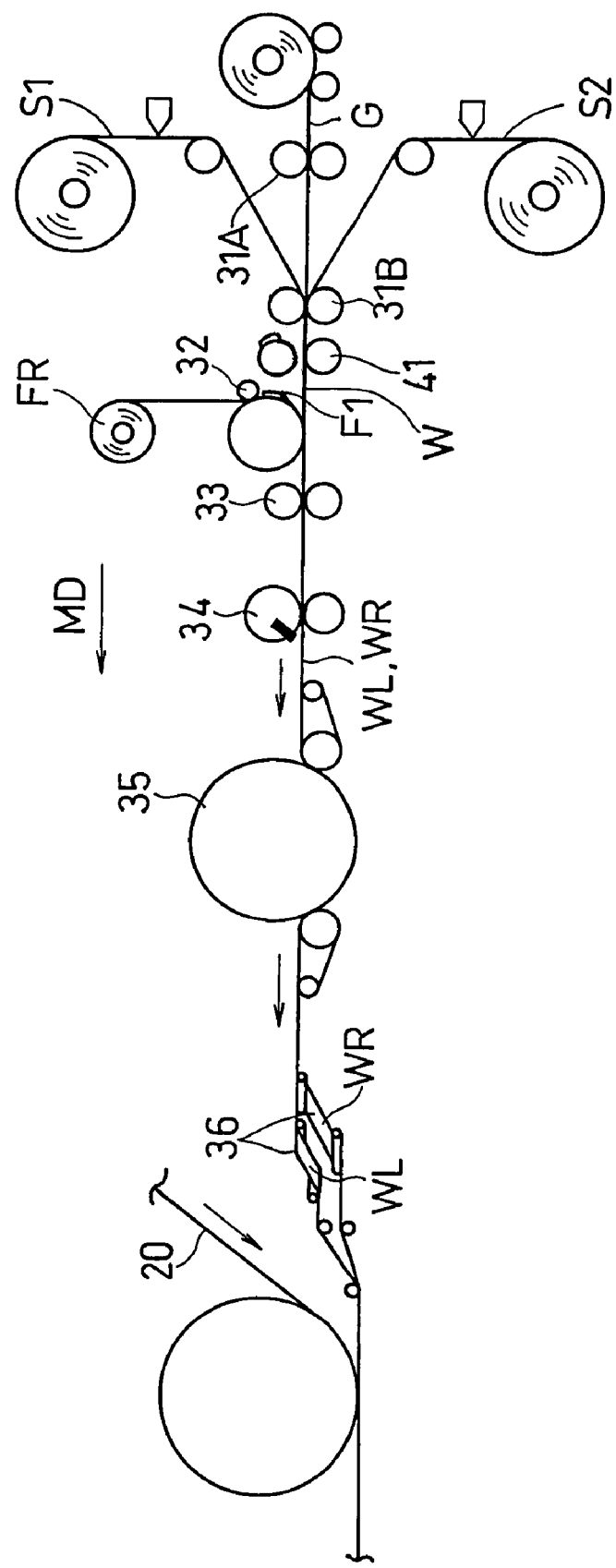
FIG. 3 is a schematic layout diagram showing a production device of the first embodiment.

FIGS. 1 to 3 show the first embodiment.

FIGS. 1(a) to 1(c) show an example of a disposable diaper of the first embodiment (an example of a worn article). FIG. 1(a) is a plan view showing a diaper being unfolded and extended, and FIG. 1(b) is a cross-sectional view taken along line Ib-Ib of FIG. 1(a).

As shown in FIG. 1(a), the diaper includes an absorbent main body portion 20, a pair of side panels PL and PR affixed to the main body portion 20, and a pair of tab members 21 and 21 affixed to the main body portion 20.

The main body portion 20, when worn, covers a front torso area (abdominal area), a crotch area and a rear torso area (back area) of the wearer. Corresponding to these areas, the main body portion 20 includes a front torso portion (abdominal portion) 20f, a crotch portion 20d and a rear torso portion (back portion) 20b.

Side Panels PL and PR:

When worn, the side panels PL and PR are each positioned between the front and rear torso portions 20f and 20b. The side panels PL and PR are affixed to the left side and the right side, respectively, of an end portion of the main body portion 20 in the longitudinal direction Y. For example, the side panels PL and PR are affixed to the rear torso portion 20b so as to protrude from the left and right of the rear torso portion 20b of the main body portion 20. Alternatively, the side panels PL and PR may be affixed to the front torso portion 20f.

The tab members 21 are affixed to the left and right of the front torso portion 20f of the main body portion 20. The tab members 21 may be omitted.

As shown in FIG. 1(b), the side panels PL and PR are formed by an elastic thread (an example of an elastic member) G sandwiched between at least two sheet-like materials S1 and S2 such as non-woven fabric sheets. As shown in FIG. 1(c), where there is no load being applied, the side panels PL and PR are in a contracted state (shrunk state) with gathers being formed as the elastic thread G contracts (shrinks) in the around-the-torso direction X.

The term "gathers (shirring)" means the shape of a sheet material being creased and contracted when there is no external force applied thereon, and includes those such as pleats and creases.

Instead of the elastic thread G, a film-shaped elastic member may be used as the elastic member for forming the gathers. The elastic member may be any material that can be sandwiched between the sheet-like materials S1 and S2 to form the gathers, and the property and the shape thereof are not limited to any particular property and shape.

Figure 14A:
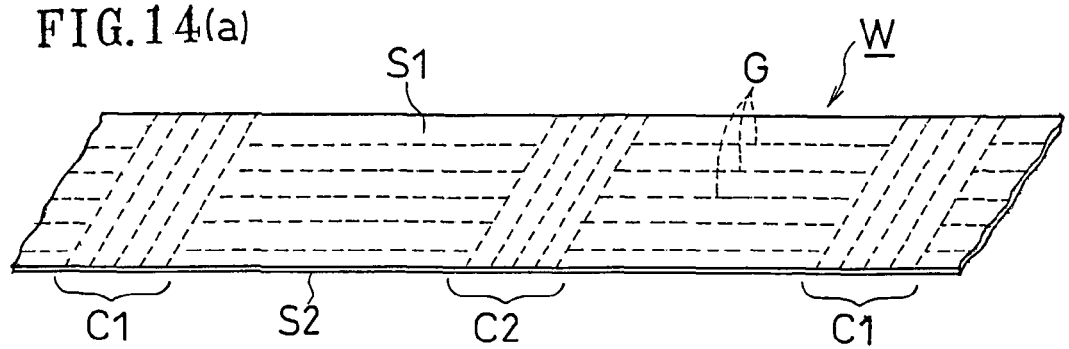
FIGS. 14(a) and 14(b) are schematic perspective views each showing an example of a laminate.
Figure 14B:
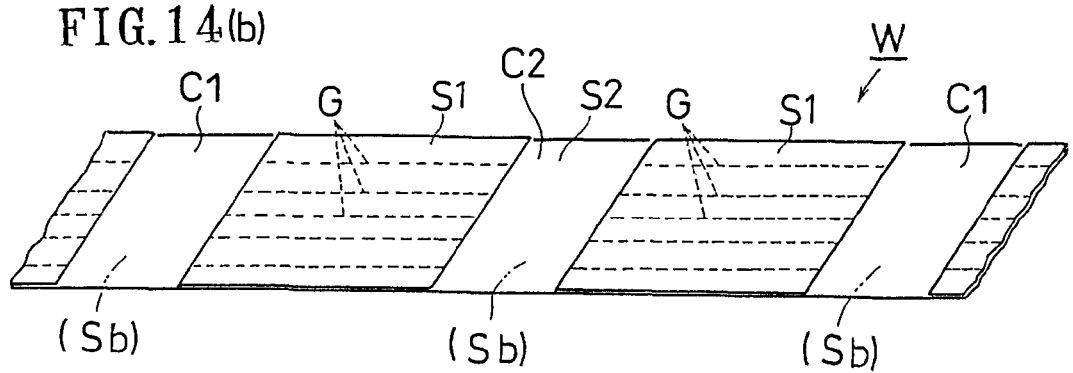

The side panels PL and PR are provided with first and second non-contractile portions C1 and C2 where the panels PL and PR are not contracted (shrunk) by the contractile force from the elastic thread G, i.e., where the contractile force from the elastic thread G does not act. As shown in FIGS. 14(a) and 14(b), the non-contractile portions C1 and C2 are formed, for example, by cutting off the elastic thread G with a pressure or by cutting the elastic thread G into small pieces with a cutter.

The first non-contractile portion C1 shown in FIG. 1 is provided at a portion of each of the side panels PL and PR where the side panel is joined to the main body portion 20, and is laid over and affixed to the main body portion 20. The second non-contractile portion C2 is provided at a tip portion of each of the side panels PL and PR in the around-the-torso direction X.

A first touch fastener (an example of the fastening element) F1 is affixed to the inner surface side (the side to be in contact with the skin when worn) of the tip portion of the second non-contractile portion C2. A second touch fastener F2, which can be touch-fastened joined detachably in face contact) to the first touch fastener F1, is affixed to the outer surface side (the side to be exposed to the outside when worn) of the main body portion 20 on the front torso portion 20f. The wearer wears the diaper by putting the side panels PL and PR around the torso of the wearer while gripping the tab members 21, and fastening the first touch fasteners F1 of the side panels PL and PR to the second touch fastener F2.

The second touch fastener F2 may be omitted. The touch fasteners may be replaced by an adhesive tape and a portion to be bonded to the adhesive tape.

Main Body Portion 20:

For example, the main body portion 20 includes a pair of cuffs (anti-leak walls) 27 to be in contact with the surface of the wearer, a liquid-permeable topsheet 24, a liquid-absorbing absorbent core 25, a liquid-impermeable backsheet 26, etc.

The main body portion 20 may include a leg elastic member 28 for forming leg gathers, for example. The cuffs 27 may be omitted, or a cuff elastic member 29 for shrinking the cuffs 27 in the Y direction may be provided. The backsheet 26 may be an air-permeable and waterproof sheet. The backsheet 26 may be a stretchable sheet.

The main body portion 20 includes such members layered (stacked) together.

Production Steps:

An example of the step of forming the side panels PL and PR and bonding them to the main body portion 20 will now be described with reference to FIG. 2.

Step of Obtaining Laminate:

First, the elastic thread G being extended is fed (supplied) between a pair of essentially non-stretchable sheet-like materials S1 and S2 along the flow direction MD of the pair of sheet-like materials S1 and S2, and the elastic thread G is sandwiched between the pair of sheet-like materials S1 and S2, thereby obtaining a laminate W to be the side panels PL and PR.

As shown in (a) of FIG. 2, the non-contractile portions C1 and C2 are formed on the laminate W alternately in the flow direction MD. The non-contractile portions C1 and C2 are spaced apart from each other. The first touch fastener F1 is bonded to the second non-contractile portion C2. The method for producing the laminate W and the method for forming the non-contractile portions will be described later.

While the elastic thread G is used herein as an example of the elastic member, a film-shaped elastic member may be used instead of the elastic thread G. The elastic member to be used instead of the elastic thread G may be any material and the property and shape thereof are not limited to any particular property and shape as long as it can be sandwiched between the sheet-like materials S1 and S2 to form gathers.

Step of Obtaining Cut Panels:

Then, the laminate W is cut at a predetermined interval in the flow direction MD to thereby obtain cut panels WL and WR adjacent to each other. In other words, a plurality of cut panels WL and WR are obtained by repeatedly cutting off a tip portion of the laminate W. The laminate W is cut off along the non-contractile portions C1 and C2. By such a cutting process, the first touch fastener F1, bonded to the second non-contractile portion C2, is cut and divided into two together while the laminate W is cut off. Therefore, one fastening element is divided into two, whereby the first touch fastener F1 is provided on each of the cut panels WL and WR.

The first touch fastener F1 may be attached to each of the cut panels WL and WR after the laminate W is cut into pieces.

Step of Changing Attitude (Turning Step):

After the cutting process, the attitude of a pair of cut panels consisting of two cut panels WL and WR adjacent to each other is changed to an attitude (orientation) that is obtained by a rotation of about 90 degrees with respect to the flow direction MD, i.e., the pair of cut panels is turned (pivoted) so that the stretch direction of the cut panel is orthogonal to the flow direction MD, as shown in (b) to (d) of FIG. 2. While the pair of cut panels WL and WR is turned by 90 degrees in the first direction in FIG. 2, the pair of cut panels WL and WR may be turned by 90 degrees in the second direction different from the first direction.

Spacing Step:

Before bonding the cut panels WL and WR (PL and PR) as shown in (h) of FIG. 2, the interval between the pair of cut panels WL and WR and the next pair of cut panels WL and WR in the flow direction MD is increased. It is only required that this spacing step is performed before the fastening step to be described later. For example, this spacing step may be performed simultaneously with, before, or after, the turning step for changing the attitude of the cut panels WL and WR. Alternatively, this spacing step may be performed simultaneously with, or after, the "step of spacing two cut panels from each other" to be described next.

Step of Spacing Two Cut Panels from Each Other:

Then, unnecessary portions 15 of the cut panels WL and WR are cut away (trimmed) as shown in (f) of FIG. 2, and the pair of cut panels WL and WR are spaced apart from each other in the CD direction generally perpendicular to the flow direction MD as shown in (g) of FIG. 2, thereby obtaining a side panel PL formed by the cut panel WL and a side panel PR formed by the cut panel RL. The trimming may be performed after the side panels PL and PR are bonded to the main body portion 20. The trimming does not always have to be performed.

Bonding Step:

Then, the first non-contractile portions C1 and C1 of the two side panels PL and PR spaced apart from each other are bonded (affixed) to the left side and the right side, respectively, of the main body portion 20 in the flow direction MD. By this bonding process, the right side panel PR (WR) and the left side panel PL (WL) are provided in the diaper.

Production Method:

An example of the method for producing the diaper will now be described with reference to FIG. 3.

The elastic thread G is introduced between a pair of drawing rolls 31A and 31B shown in FIG. 3. The drawing rolls 31 (31A and 31B) draw the elastic thread G in the flow direction MD. The drawing process is performed by, for example, setting the circumferential velocity of the drawing roll 31B to a value greater than the circumferential velocity of the upstream drawing roll 31A. The draw ratio is preferably set to about 2.0 to 4.5.

Then, the elastic member G being drawn is sandwiched between, and bonded to, non-woven fabric sheets S1 and S2, thus obtaining the laminate W. The bonding can be done by using a hot-melt adhesive, ultrasonic welding, etc. Then, a part of the elastic member G of the laminate W is cut into small pieces by an embossing roll 41, or the like, to deactivate the contraction stress of the part of the elastic member G, thus forming the first and second non-contractile portions C1 and C2.

Then, the first touch fastener F1 is bonded to the second non-contractile portion C2 of the laminate W ((a) of FIG. 2). The first touch fastener F1 is obtained by drawing out a material from a fastener roll FR and then cutting the material to a predetermined length by a fastener cutter 32.

After the bonding process, the laminate W is introduced into a pair of relaxing rolls 33 to form the gathers. The gathers (the portion of each cut panel of FIG. 1 between the first and second non-contractile portions C1 and C2) are formed because of the contraction of the elastic thread G of the laminate W due to the circumferential velocity of the relaxing rolls 33 being set to a value smaller than the circumferential velocity of the upstream drawing rolls 31.

Then, the laminate W is cut off by a cutter 34 to obtain the cut panels WL and WR shown in (a) of FIG. 2.

After the cutting process, an adjustment drum 35 changes the attitude of a pair of cut panels consisting of two cut panels WL and WR adjacent to each other to an attitude that is obtained by a rotation of about 90 degrees with respect to the flow direction MD (turning step), and increases the interval between the pair of cut panels WL and WR and the next (subsequent) pair of cut panels WL and WR (spacing step).

The drum 35 receives the pair of cut panels WL and WR onto a pad thereof, and the pad rotates around the drum 35 while increasing the circumferential velocity thereof so as to increase the interval between pads and turning about an axis generally in the diameter direction of the drum 35. This increases the interval between pairs of cut panels WL and WR in the flow direction MD while turning each pair of cut panels WL and WR, as shown in (b) to (e) of FIG. 2. Thus, the attitude of the pair of cut panels WL and WR is changed to an attitude that is obtained by a 90 degrees rotation.

In a case where the turning step and the spacing step are performed separately, the following structure can be used.

The structure and method for performing the spacing step may be, for example, those disclosed in Japanese Laid-Open Patent Publication No. 2002-345889.

The structure for performing the turning step may be, for example, any of various structures such as those disclosed in Japanese Laid-Open Patent Publication No. 63-317576, Japanese Patent Examined Publication No. 07-051143, and Japanese Laid-Open Patent Publication No. 2003-199790 (Paragraphs 0021 to 0024 and FIG. 2).

Then, an interval-increasing device 36 spaces apart each pair of cut panels WL and WR from each other in the CD direction ((f) of FIG. 2), thus obtaining the side panels PL and PR.

After this spacing process, the side panels PL and PR are bonded to the left side and the right side, respectively, of the main body portion 20, which is supplied from a separate line.

The tab members 21 may be bonded to the main body portion 20 before the bonding of the side panels PL and PR or may be bonded to the main body portion 20 after the bonding of the side panels PL and PR.

Modified Embodiment

Another method for obtaining a diaper of the first embodiment as described above will now be described.

Figure 5:
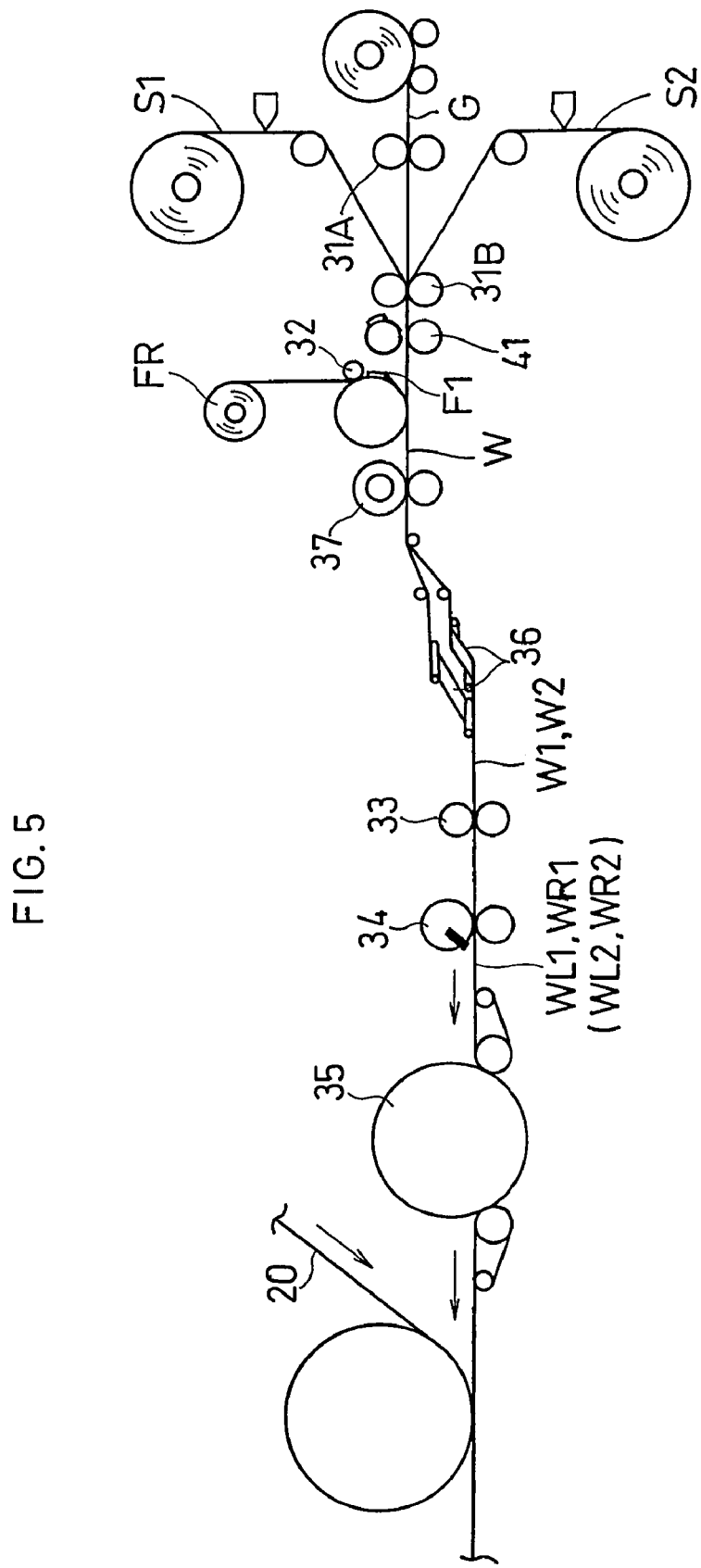
FIG. 5 is a schematic layout diagram showing a production apparatus of the modified embodiment.

FIGS. 4 and 5 show a modification of the embodiment.

As shown in (a) of FIG. 4, after the first touch fastener F1 is bonded to the second non-contractile portion C2, the laminate W is cut (slit) along a generally straight cut-off line extending in the flow direction MD. Thus, the laminate W is divided into the first and second laminates W1 and W2, which are separated from each other in the width direction CD (the direction generally perpendicular to the flow direction MD). Then, the first and second laminates W1 and W2 are spaced apart from each other in the width direction CD. The first touch fastener F1 may be bonded to each of the laminates W1 and W2 after the slitting process. After the spacing process, the two slit laminates W1 and W2 are cut off at a predetermined interval in the flow direction MD, i.e., repeatedly cutting off a tip portion of each of the laminates W1 and W2, thus obtaining left and right cut panels WL1 and WR1 (WL2 and WR2).

Then, as shown in (b) to (d) of FIG. 4, each of the cut panels WL1 and WR1 is turned by about 90 degrees, thereby changing the attitude of each of the cut panels WL1 and WR1 to be orthogonal with respect to the flow direction MD. The left and right cut panels WL1 and WR1 are rotated by about 90 degrees in different directions, while increasing the interval between the pair of left and right cut panels WL1 and WR1 and the next pair of left and right cut panels WL2 and WR2.

Then, the spacing step and the bonding step as shown in (f) to (h) of FIG. 2 are performed.

As shown in FIGS. 4(f) to 4(h), each of the next pair of cut panels WL2 and WR2 are rotated by about 90 degrees in opposite directions to the previous cut panels WL1 and WR1, respectively.

Production Method of the Modified Embodiment

As shown in FIG. 5, after the first touch fastener F1 is bonded to the laminate W, the laminate W is cut (slit) by a slitter 37 to obtain the first and second laminates W1 and W2 shown in (a) of FIG. 4. Then, the interval between the first and second laminates W1 and W2 in the width direction CD is increased by the interval-increasing device 36. In other words, the laminates W1 and W2 are spaced apart from each other in the width direction CD.

There are provided a pair of (two lines of) each of the relaxing rolls 33, the cutters 34 and the adjustment drums 35 for processing the first and second laminates W1 and W2.

The laminates W1 and W2 whose interval has been increased are relaxed by the relaxing rolls 33, and then cut by the cutters 34, to produce the cut panels WL1 and WR1.

The adjustment drums 35 increase the interval between the left and right cut panels WL1 and WR1 and the next pair of left and right cut panels WL2 and WR2, while rotating the left and right cut panels WL1 and WR1 by about 90 degrees in the first and second directions R1 and R2 ((b) of FIG. 4), respectively, thus changing the attitude of each of the cut panels WL1 and WR1 to be orthogonal with respect to the flow direction MD.

Then, the adjustment drums 35 increase the interval between the next pair of cut panels WL2 and WR2 and the second next pair of cut panels, while rotating the left and right cut panels WL2 and WR2 by about 90 degrees in the second and first directions R2 and R1, respectively, thus changing the attitude of each of the cut panels WL2 and WR2. The rotation direction R2 of the cut panel WL2 is opposite to the rotation direction R1 of the previous cut panel WL1, and the rotation direction R1 of the cut panel WR2 is opposite to the rotation direction R2 of the previous cut panel WR1. A mechanism for increasing the interval between the cut panels WL1 and WL2 (WR1 and WR2) while rotating the cut panels WL1 and WL2 (WR1 and WR2) in the forward direction and in the reverse direction (in opposite directions) will be described later.

Second Embodiment

Figure 6:
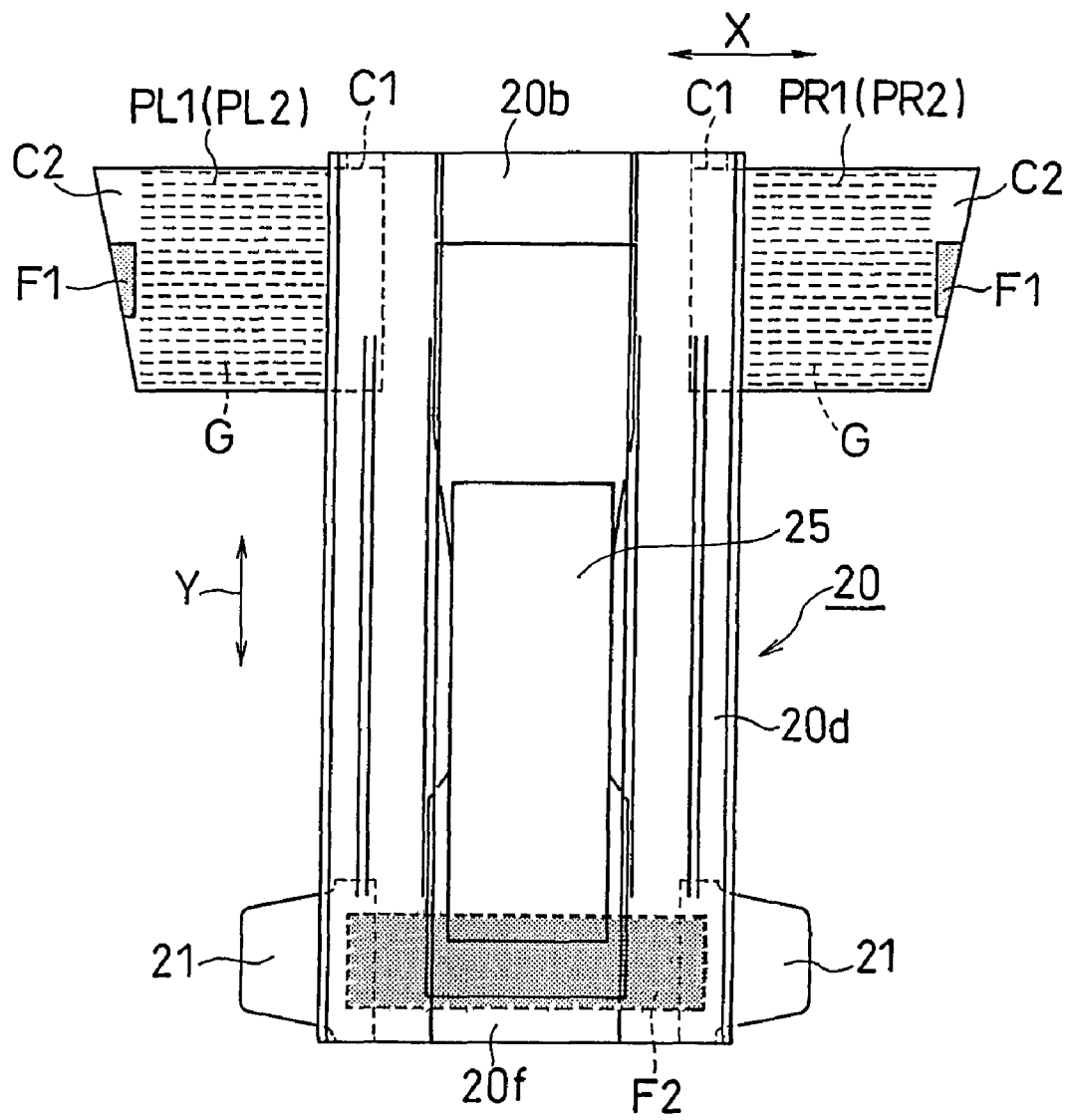
FIG. 6 is a schematic plan view showing a worn article in an extended state according to the second embodiment.
Figure 7:
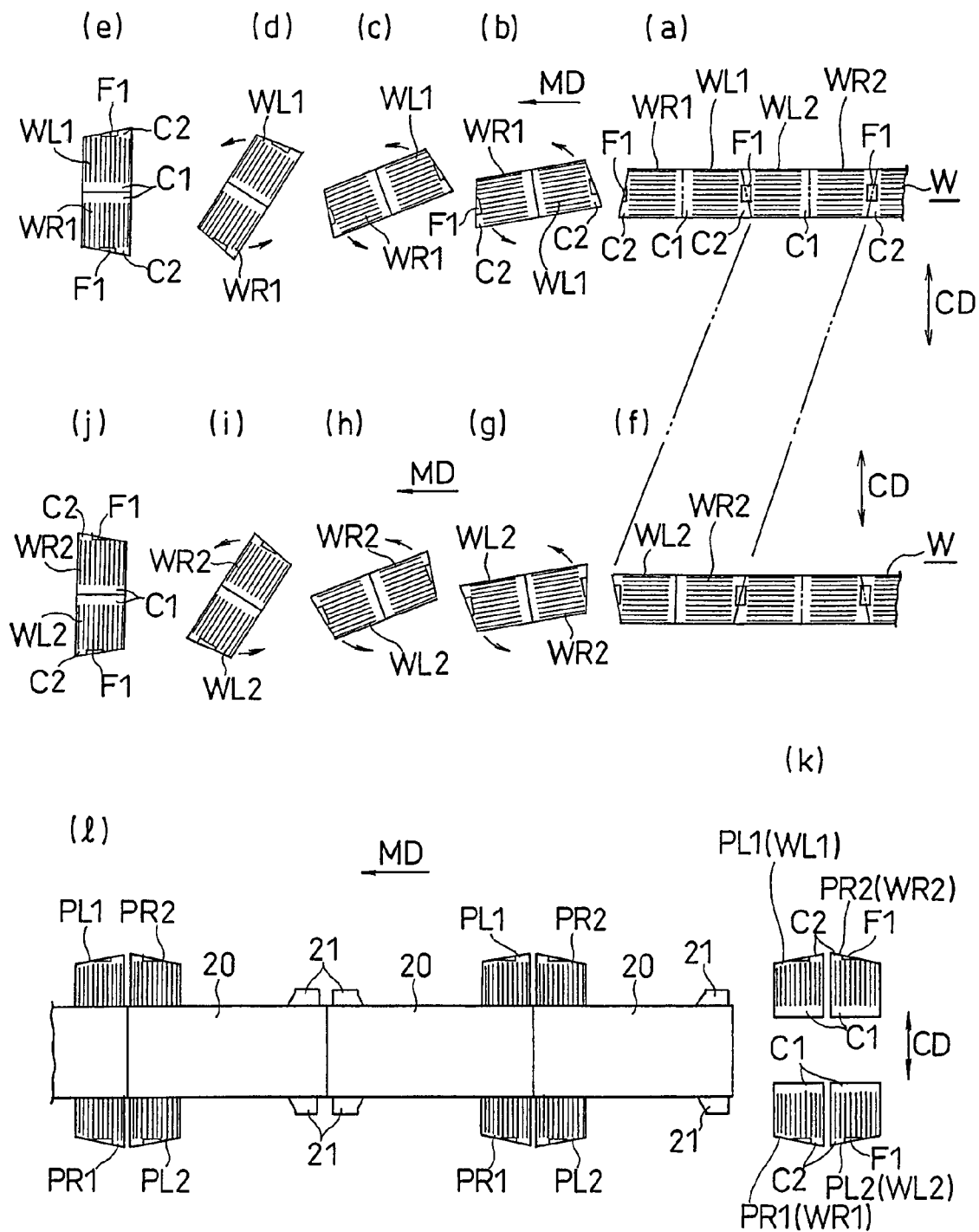
FIG. 7 is a process diagram showing a production process of the second embodiment.

FIGS. 6 and 7 show the second embodiment.

In the above-described first embodiment, a trimming process is performed when producing the cut panels to remove the unnecessary portions 15. The second embodiment and subsequent embodiments are directed to methods for producing cut panels that do not require the trimming process (i.e., methods without loss).

As shown in FIG. 6, in the side panels PL1 and PR1 (PL2 and PR2) of the second embodiment, the second non-contractile portion C2 is cut in a slant direction with respect to the Y direction. Other than this, the embodiment is similar to the first embodiment. Therefore, the same or like elements corresponding to those of the first embodiment will be denoted by the same reference numerals as the first embodiment and will not be further described below.

Production steps will now be described with reference to FIG. 7.

As shown in (a) of FIG. 7, after the first touch fastener F1 is bonded to the second non-contractile portion C2, the laminate W is cut at a predetermined interval in the flow direction MD, thereby obtaining a pair of cut panels consisting of two cut panels WL1 and WR1 adjacent to each other. The laminate W is cut in the second non-contractile portion C2 along a slant cut-off line that is slant with respect to the width direction CD. The cut-off line of the second non-contractile portion C2 and the cut-off line of another adjacent second non-contractile portion C2 are inclined in opposite directions with respect to a line extending in the width direction CD. Thus, a pair of cut panels WL1 and WR1 and another pair of cut panels WL2 and WR2 upside down of the first pair are formed alternately.

Then, as shown in (b) to (e) of FIG. 7, after being spaced apart from the subsequent cut panels WL2 and WR2, the cut panels WL1 and WR1 are turned by about 90 degrees, thereby changing the attitude of each of the cut panels WL1 and WR1 to be orthogonal to the flow direction MD. After the turning process, the two cut panels WL1 and WR1 are spaced apart from each other in the width direction CD as shown in (k) of FIG. 7.

As shown in (f) to (j) of FIG. 7, the subsequent pair of cut panels WL2 and WR2 are also turned by 90 degrees in the same direction, thereby changing the attitude of each of the cut panels WL2 and WR2. Then, the two cut panels WL2 and WR2 are spaced apart from each other in the width direction CD.

As shown in (l) of FIG. 7, the interval between a set of two pairs of cut panels WL1-WR1 and WL2-WR2 (PL1-PR1 and PL2-PR2) and another set of two pairs of cut panels is increased, and then the cut panels are bonded to the main body portion 20.

By the bonding process, the right side panels PR1 and PR2 (WR1 and WR2) and the left side panels PL1 and PL2 (WL1 and WL2) are formed in the diaper.

The apparatus for producing the diaper of the second embodiment may be the production apparatus of FIG. 3, for example.

A modification of the second embodiment will now be described.

Figure 8:
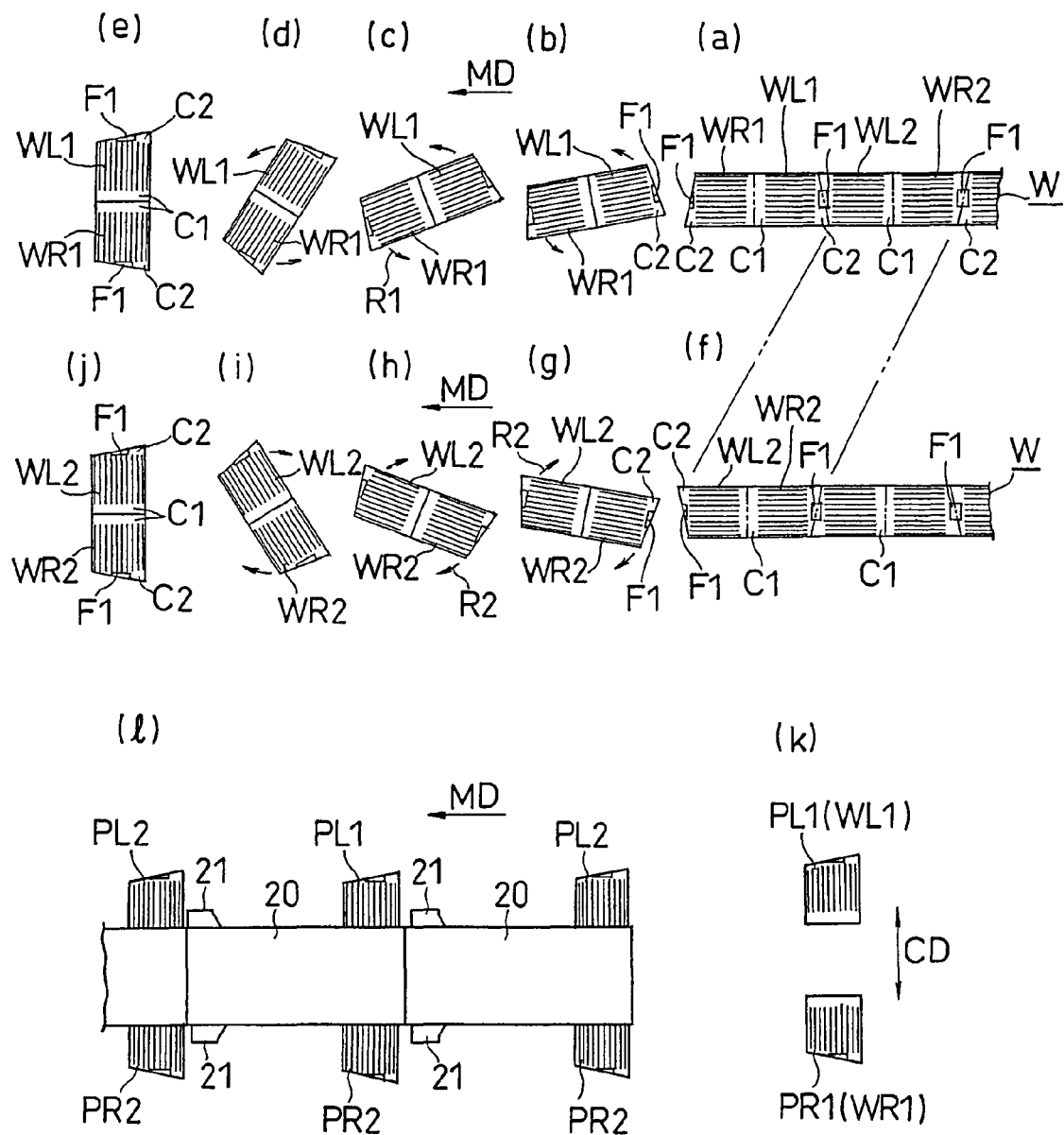
FIG. 8 is a process diagram showing a production process of a modified embodiment.

As shown in FIG. 8, a pair of cut panels WL1 and WR1 and the subsequent pair of cut panels WL2 and WR2 may be turned in the opposite directions R1 and R2.

Figure 9:
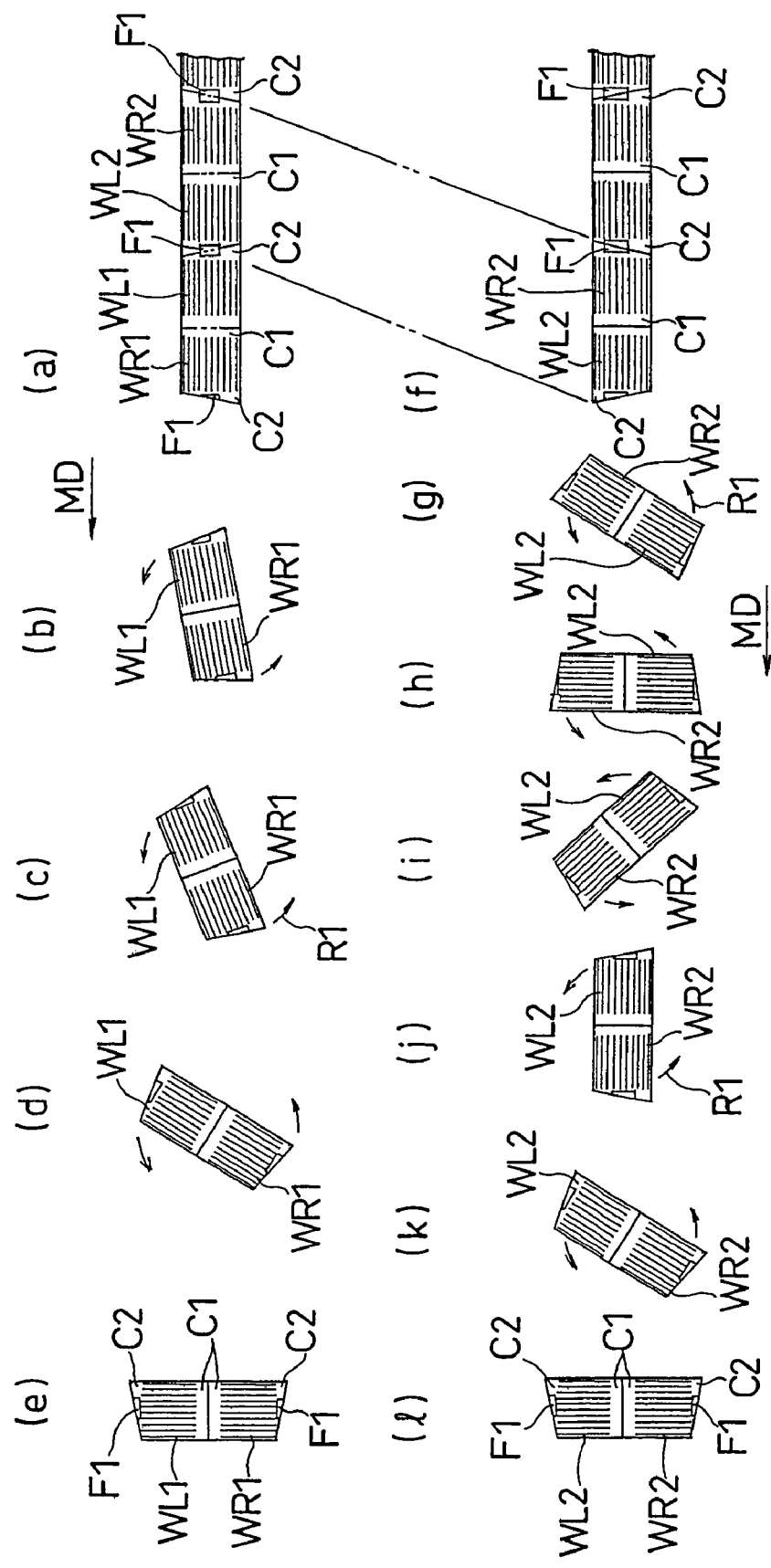
FIG. 9 is a process diagram showing a production process of a modified embodiment.

As shown in FIG. 9, a pair of cut panels WL1 and WR1 may be turned by 90 degrees in the first direction R1, while turning the subsequent pair of cut panels WL2 and WR2 by 270 degrees in the first direction R1.

Third Embodiment

Figure 10:
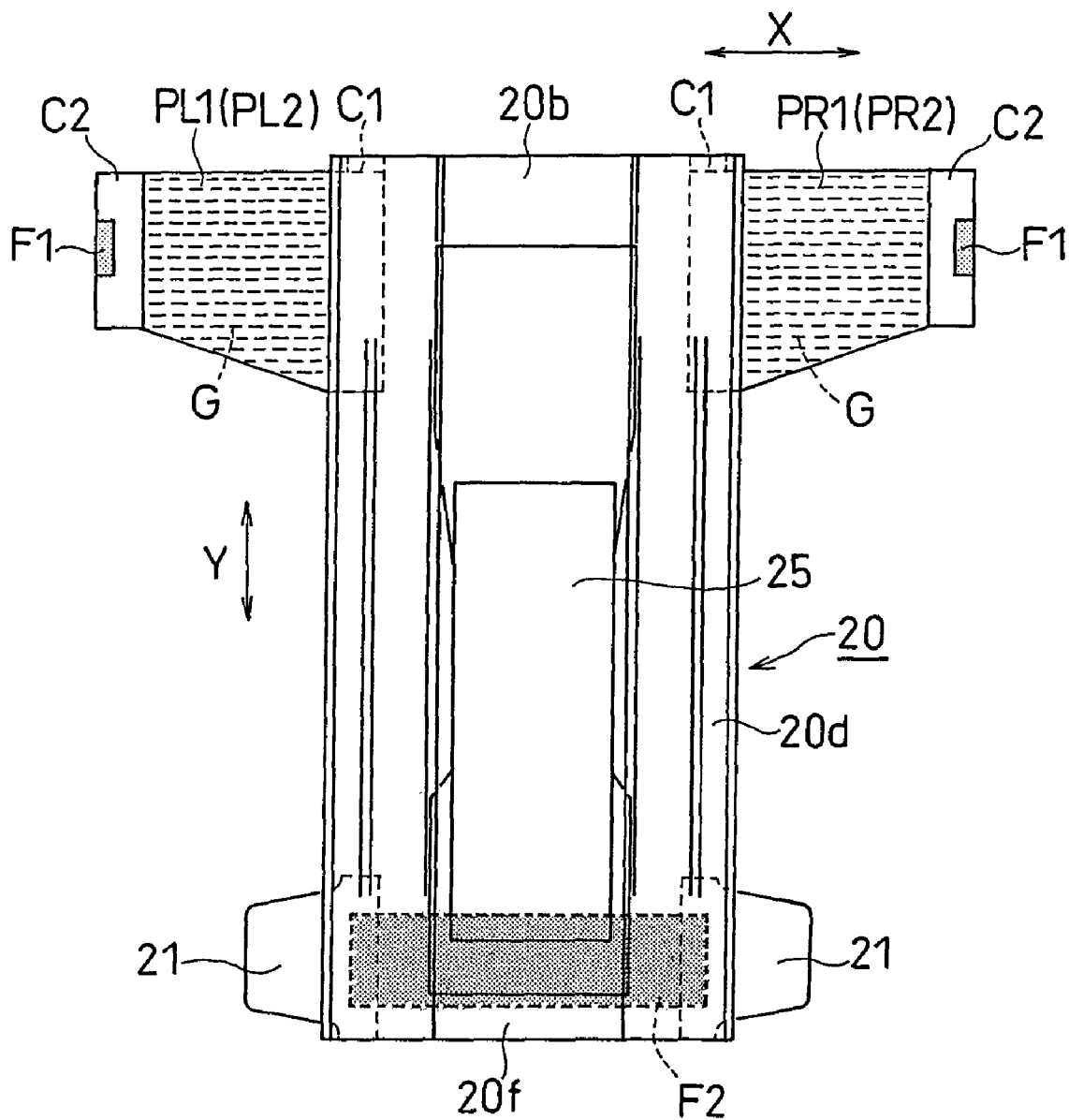
FIG. 10 is a schematic plan view showing a worn article in an extended state according to the third embodiment.
Figure 11:
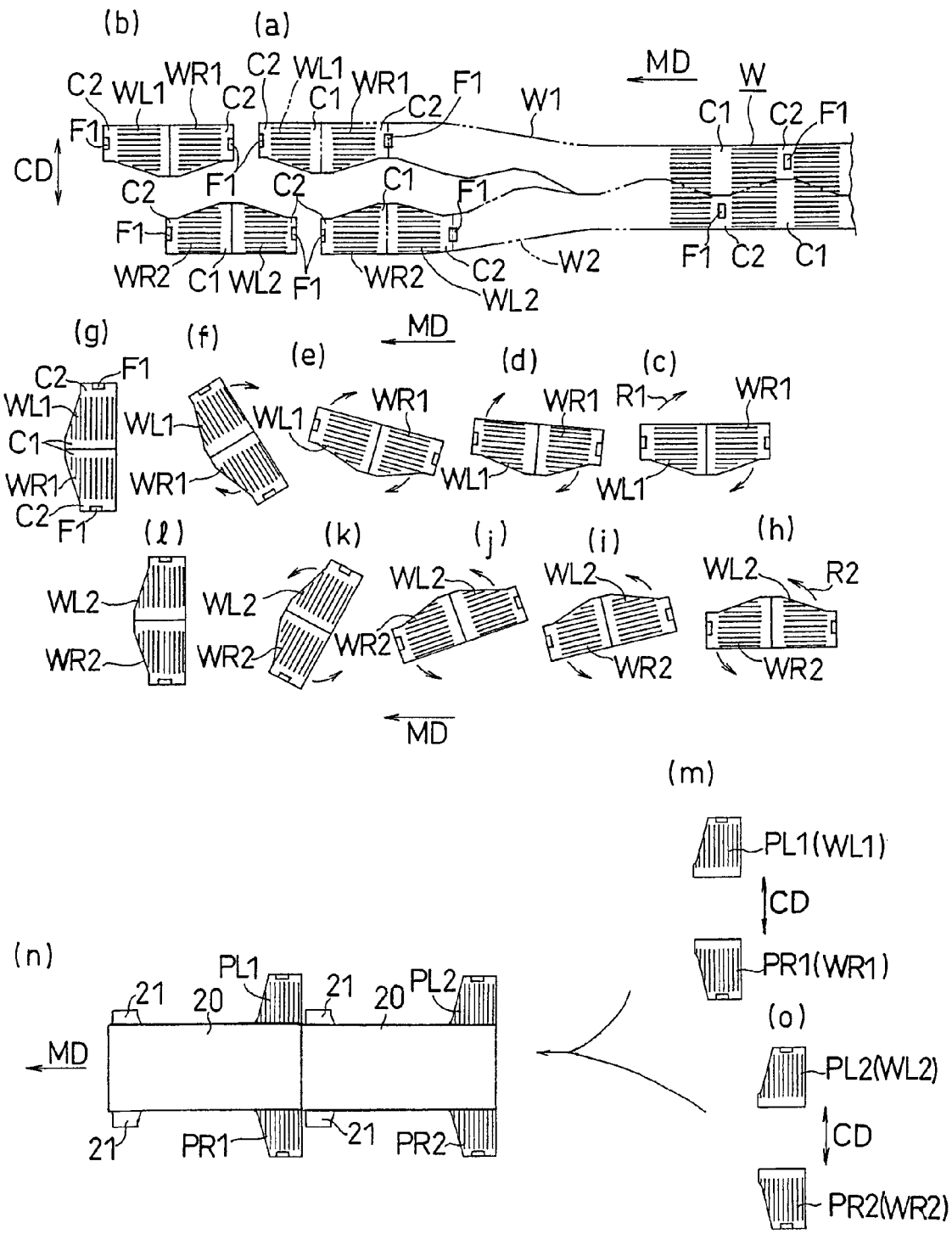
FIG. 11 is a process diagram showing a production process of the third embodiment.
Figure 12:
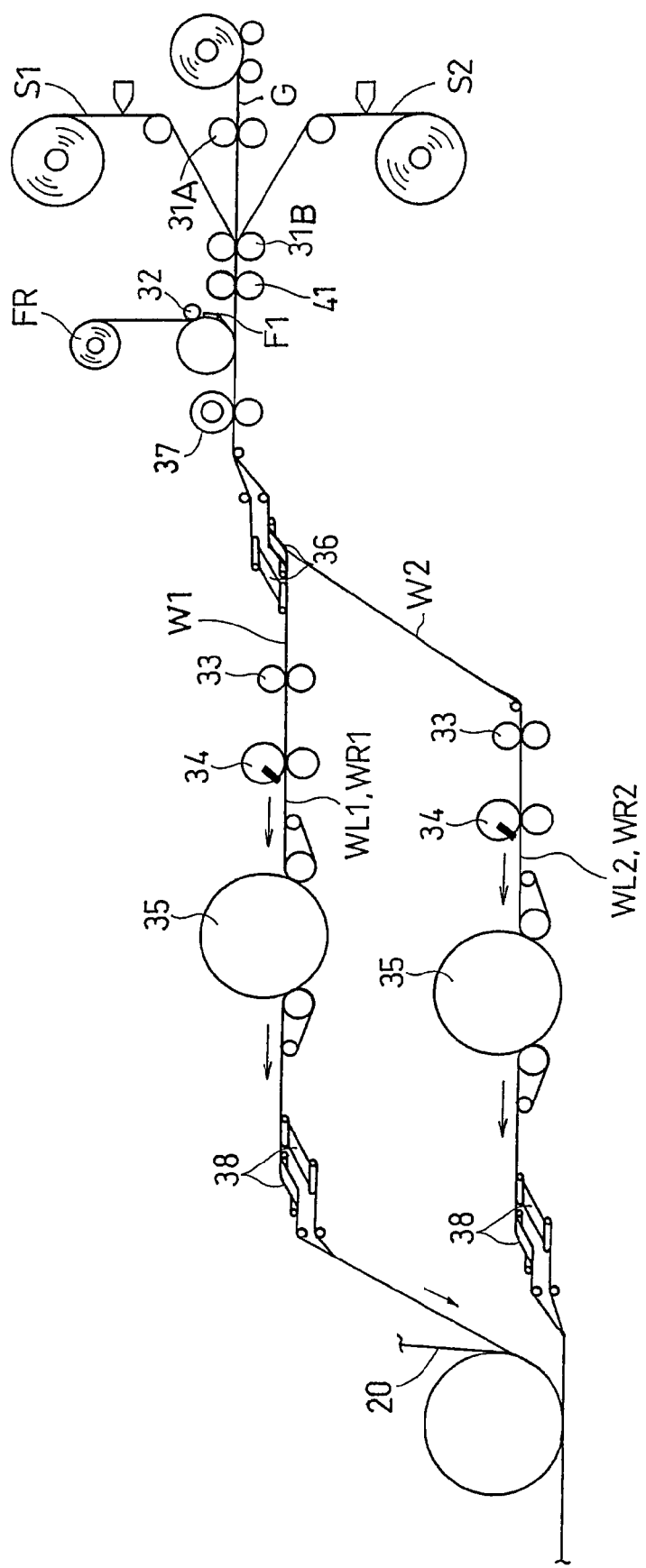
FIG. 12 is a schematic layout diagram showing a production apparatus of the third embodiment.

FIGS. 10 to 12 show the third embodiment.

As shown in FIG. 10, with the side panels PL1 and PR1 (PL2 and PR2) of the third embodiment, the contractile portion between the first non-contractile portion C1 and the second non-contractile portion C2 is partially cut off in a slant direction with respect to the X direction. Thus, the width of each of the two side panels PL1 and PR1 in the Y direction gradually decreases (i.e., the height thereof decreases) from the first non-contractile portion C1 toward the second non-contractile portion C2. Other than this, this embodiment is similar to the first embodiment. Therefore, the same or like elements corresponding to those of the first embodiment will be denoted by the same reference numerals as the first embodiment and will not be further described below.

Production steps will now be described with reference to FIG. 11.

In the production steps of the diaper of the third embodiment, two processing lines are used to produce two pairs of cut panels each time as will be described below.

As shown in (a) of FIG. 11, after the first touch fastener F1 is bonded to the second non-contractile portion C2, the laminate W is cut along the cut-off line extending in the flow direction MD, thereby obtaining the first and second laminates W1 and W2, which are separated from each other in the width direction CD. The laminate W is slit (i.e., divided in the width direction) along a predetermined wave-shaped cut-off line extending in the flow direction MD such that peaks and troughs alternate with each other. Then, the first and second laminates W1 and W2, which have been separated from each other, are spaced apart from each other in the width direction CD. While the cut-off line in FIG. 11 has an angular wave shape, the cut-off line may be a smoothly continuous and generally S-shaped wavy line.

By slitting the material along a wave shape (generally S-letter shape), it is possible to obtain a disposable diaper with an improved fit and an improved aesthetic quality with little or no trim waste (loss).

After the spacing process, the laminates W1 and W2, which have been formed by slitting the material into two, are cut off at a predetermined interval in the flow direction MD (i.e., repeatedly cutting off a tip portion of each of the laminates W1 and W2), thereby obtaining a pair of cut panels WL1 and WR1 (WL2 and WR2) consisting of two cut panels adjacent to each other as shown in (b) of FIG. 11. In this process, each pair of cut panels are separated (divided) at the second non-contractile portion C2 forming the trough portion from the subsequent pair of cut panels. Thus, in a pair of cut panels WL1 and WR1 (WL2 and WR2), the first non-contractile portions C1 and C1 forming the peak portion, are adjacent to each other. Therefore, the up-down orientation of a pair of first cut panels WL1 and WR1 produced from the first laminate W1 is opposite to that of a pair of second cut panels WL2 and WR2 produced from the second laminate W2. Specifically, the first cut panels WL1 and WR1 are positioned so that the peak portion of the first cut panels WL1 and WR1 is facing downward in (a) of FIG. 11, and the second cut panels WL2 and WR2 are positioned so that the peak portion of the second cut panels WL2 and WR2 is facing upward in (a) of FIG. 11.

Then, as shown in (c) to (g) of FIG. 11, the interval between the pair of first cut panels WL1 and WR1 and the subsequent pair of first cut panels is increased, and the pair of first cut panels WL1 and WR1 are turned by about 90 degrees, thereby changing the attitude thereof to be orthogonal to the flow direction MD. In this process, the first cut panels WL1 and WR1 are turned in the first direction R1. After the turning process, the two first cut panels WL1 and WR1 are spaced apart from each other in the width direction CD as shown in (m) of FIG. 11. After this spacing process, the first cut panels WL1 and WR1 (PL1 and PR1) are bonded to the main body portion 20 as shown in (n) of FIG. 11.

As shown in (h) to (l) of FIG. 11, the interval between the pair of second cut panels WL2 and WR2 and the subsequent pair of cut panels is increased, and the pair of second cut panels WL2 and WR2 are turned by about 90 degrees in the second direction R2, which is opposite to the turning direction R1 of the pair of the first cut panels WL1 and WR1. After the turning process, the two second cut panels WL2 and WR2 are spaced apart from each other in the width direction CD as shown in (o) of FIG. 11. After this spacing process, the second cut panels WL2 and WR2 (PL2 and PR2) are bonded to the main body portion 20 as shown in (n) of FIG. 11.

A method for producing a diaper of the present embodiment will now be described briefly with reference to FIG. 12.

As shown in FIG. 12, after the first touch fastener F1 is bonded to the laminate W, the laminate W is slit by the slitter 37, thereby obtaining the first and second laminates W1 and W2 shown in (a) of FIG. 11. Then, a first interval-increasing device 36 increases the interval between the first and second laminates W1 and W2 in the width direction CD.

As shown in FIG. 12, there are provided a pair of (two lines of) each of the slackening rolls 33, the cutters 34 and the adjustment drums 35.

In the first line, the first laminate W1, which has been spaced away from the second laminate W2, is relaxed by the relaxing rolls 33, and then cut by the cutter 34, to produce the first cut panels WL1 and WR1.

Then, the adjustment drum 35 increases the interval between a pair of first cut panels WL1 and WR1 and the next pair of cut panels, and rotates the pair of first cut panels WL1 and WR1 by about 90 degrees in the first direction R1, thus changing the attitude thereof to be orthogonal to the flow direction MD. After the interval between the first cut panels WL1 and WR1 is increased by a second interval-increasing device 38, the first cut panels WL1 and WR1 are bonded to the main body portion 20.

In the second line, a similar processing to that of the first laminate W1 is performed for the second laminate W2 to produce the second cut panels WL2 and WR2, which are then bonded to the main body portion 20. The adjustment drum 35 increases the interval between a pair of second cut panels WL2 and WR2 and the next pair of second cut panels, while rotating the pair of second cut panels WL2 and WR2 by about 90 degrees in the second direction R2, which is opposite to the rotation direction R1 of the pair of the first cut panels WL1 and WR1, thus changing the attitude thereof.

Figure 13:
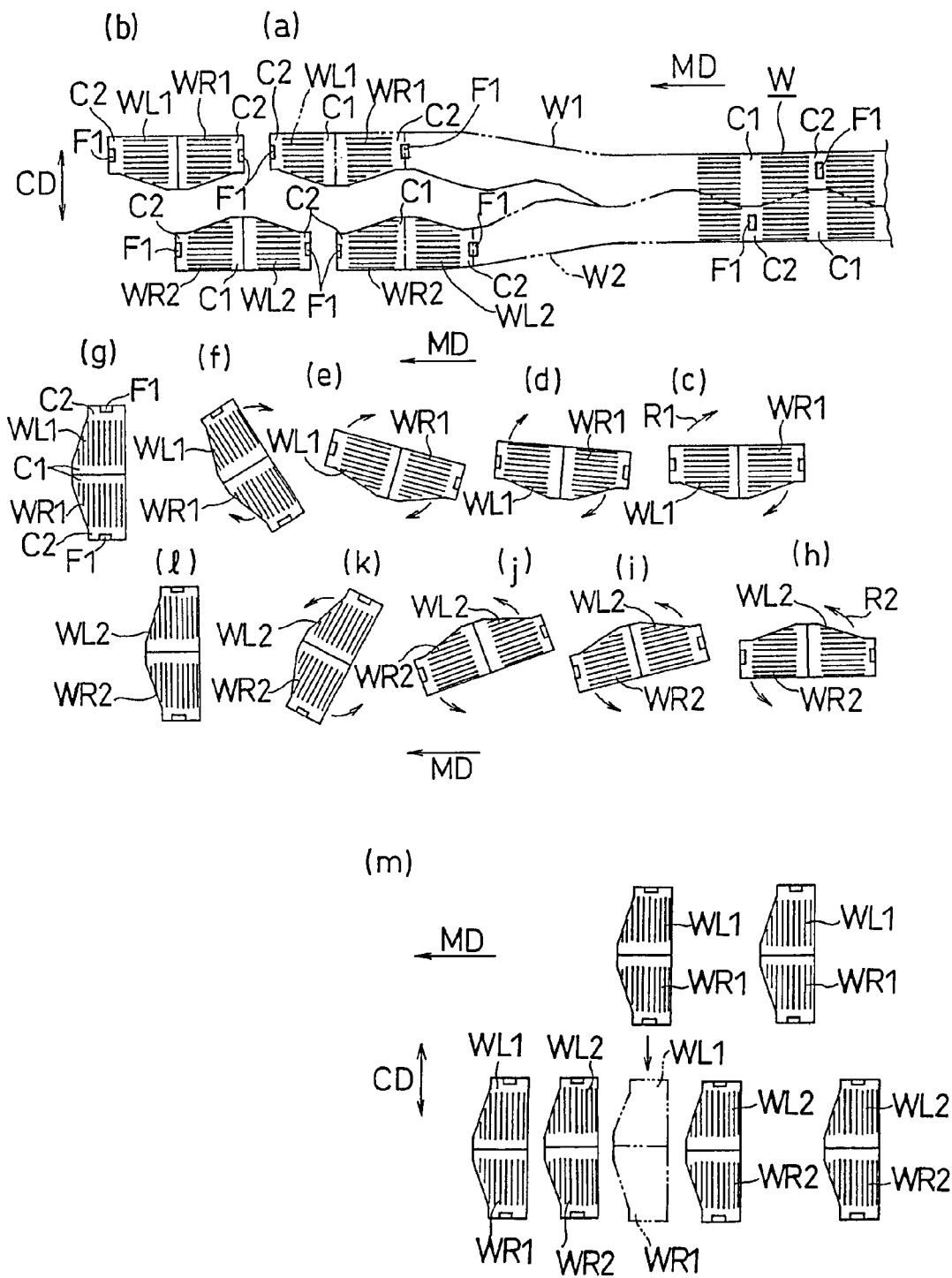
FIG. 13 is a process diagram showing a production process of a modified embodiment.

FIG. 13 shows a modification.

As shown (m) of in FIG. 13, the pair of the first cut panels WL1 and WR1 may be moved to the line of the pair of the second cut panels WL2 and WR2 so as to align both pairs of cut panels with each other. Such movement may be realized by, for example, moving pads, which carry cut panels thereon, around a drum.

Steps of (a) to (l) of FIG. 13 are similar to those of (a) to (l) of FIG. 11, and will not be further described below.

Method for Producing Laminate W:

A method for producing the laminate W will now be described.

The laminate W shown in FIG. 14(a) includes the non-stretchable portions C1 and C2 where the elastic thread G between the sheet-like materials S1 and S2 has been cut off by an embossing process.

Such a laminate W is produced in the following way: first, the sheet-like materials S1 and S2 are bonded together with the elastic thread G in an extended state being sandwiched therebetween; then, only the elastic thread G is cut off by performing an embossing process with the emboss roll heated to room temperature or a predetermined temperature, or by using a cutter, or the like. Portions where the elastic thread G is cut off by the embossing process, or the like, become the non-stretchable portions C1 and C2.

Figure 15:
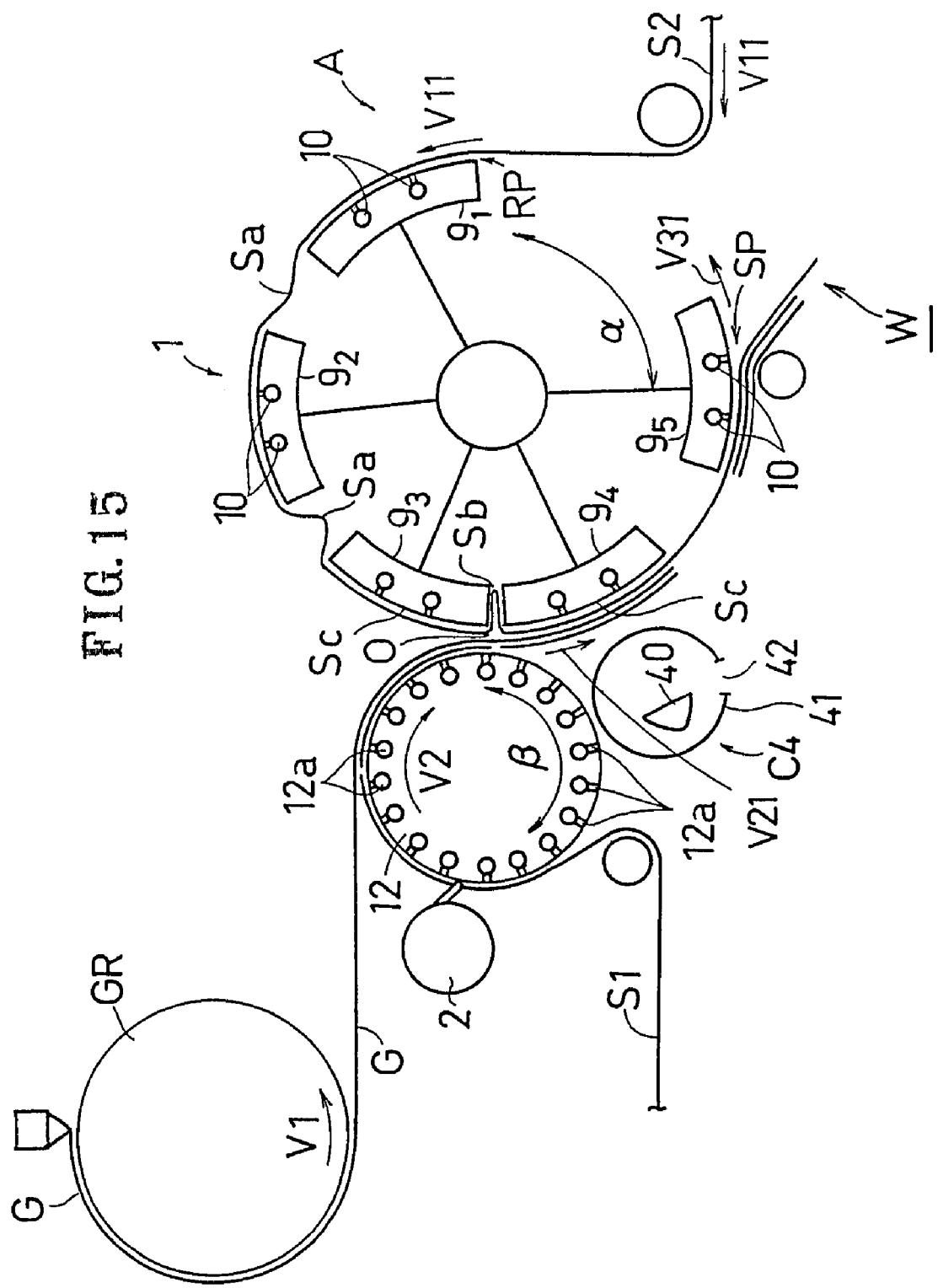
FIG. 15 is a schematic layout diagram showing a device for producing the laminate.

The laminate W shown in FIG. 14(b) can be produced by, for example, a production device shown in FIG. 15.

Figure 14C:
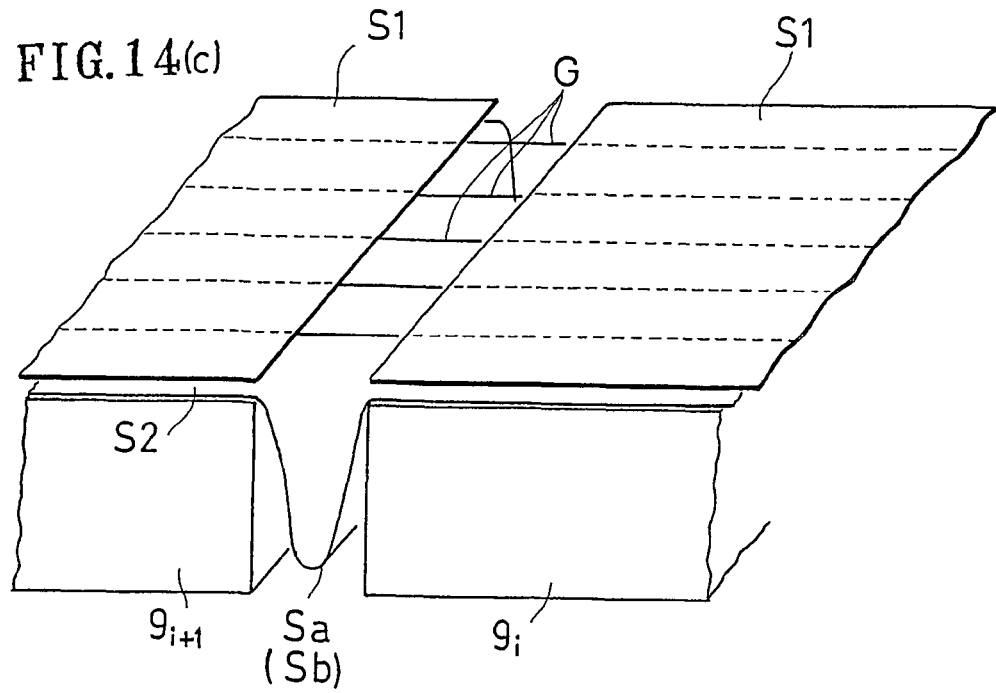
FIG. 14(c) is a schematic perspective view showing a method for producing the laminate of FIG. 14(b).

The production device shown in FIG. 15 includes a rotating device 1 capable of relaxing the second sheet-like material S2, and a second roll 12 capable of placing the elastic thread G in a portion other than a portion where the second sheet-like material S2 is relaxed. The elastic thread G extending over a slack portion of the second sheet-like material S2 is cut off by a cutter C4 of FIG. 15, e.g., at least one of laser, industrial light, a blade and scissors, after it is placed so as to extend over the slack portion as shown in FIG. 14(c). Thus, the present device is capable of placing the elastic thread G intermittently onto the second sheet-like material S2. The intermittent pattern is caused primarily by the slack of the second sheet-like material S2.

In FIG. 15, the elastic thread G of a first roll GR is fed to the second roll 12. The circumferential velocity V2 of the second roll 12 is set to a value larger than the circumferential velocity V1 of the first roll GR. Thus, the elastic thread G is extended between the first roll GR and the second roll 12.

The first sheet-like material S1 is fed to the second roll 12. The second roll 12 carries the first sheet-like material S1 while sucking it by a vacuum, or the like. The surface of the second roll 12 may include, for example, many suction holes 12a for sucking the first sheet-like material S1. After the first sheet-like material S1 is sucked and held on the surface of the second roll 12 by a vacuum, or the like, the first sheet-like material S1 is divided into pieces of a predetermined size by a web cutter 2.

After the division process, the elastic thread G is placed so as to extend over the surface of the divided first sheet-like material S1. An adhesive is applied on at least one of the elastic thread G, the first sheet-like material S1 and the second sheet-like material S2.

The rotating device 1 for performing a folding process is placed near the second roll 12.

The rotating device 1 includes a plurality of pads $9i$ capable of sucking the second sheet-like materials S2 and carrying the second sheet-like materials S2. Suction holes 10 for sucking the second sheet-like material S2 are provided on the surface of each pad $9i$. The rotating device 1 continuously carries sheet-like materials. The first sheet-like material S1, the elastic thread G and the second sheet-like material S2 are in contact with one another at the contact point O, thus producing the laminate W.

At the receiving position RP, the rotating device 1 receives the second sheet-like material S2 at the velocity V11. At the point A where a pad 9i receives the second sheet-like material S2, the circumferential velocity of the pad is V11. The rotation velocity of each pad 9i, which is the velocity V11 at the point A, is decreased to the velocity V21 while the pad 9i moves toward the contact point O. Therefore, the interval between the pads 9i is decreased from the receiving position RP to the contact point O. Thus, the second sheet-like material S2 is slackened between the pads 9i to form a slack portion Sa.

Attitude-Changing Device:

A device and method for the attitude-changing process will now be described.

Figure 16:
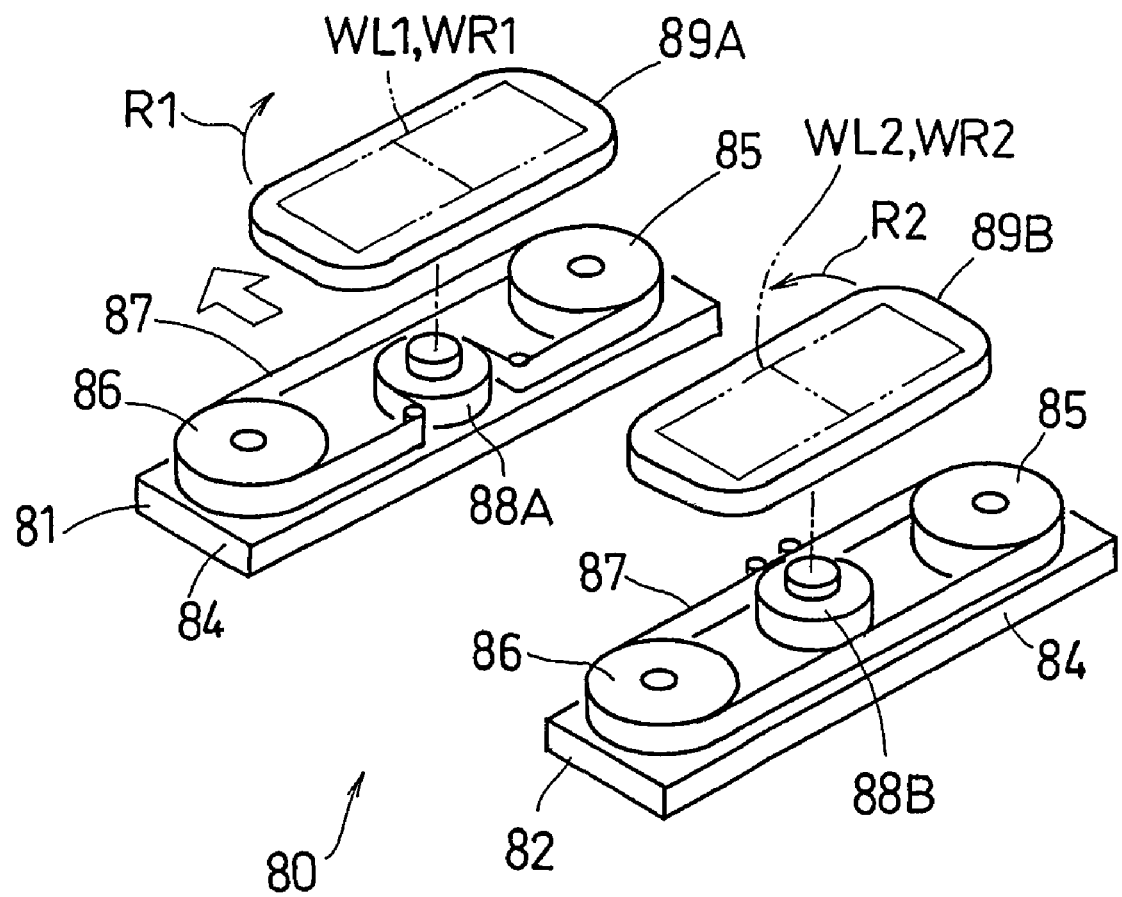
FIG. 16 is a perspective view showing an example of an attitude-changing device.

In FIG. 16, an attitude-changing device 80 includes first moving sections 81 and second moving sections 82 in an alternating pattern on an adjustment drum (not shown). The adjustment drum is provided with a guide groove 83 shown in FIGS. 17(*a*) to 17(*e*).

In FIG. 16, the first and second moving sections 81 and 82 each have a pad base 84 rotating in the circumferential direction of the adjustment drum. A drive pulley 85 and a driven pulley 86 are rotatably provided on the pad base 84. A timing belt 87 is wound around the pulleys 85 and 86. A circumscribed pulley 88A is engaged with the timing belt 87 of the first moving section 81, and an inscribed pulley 88B is engaged with the timing belt 87 of the second moving section 82. First and second pads 89A and 89B are mounted on the circumscribed pulley 88A and the inscribed pulley 88B, respectively.

Figure 17:
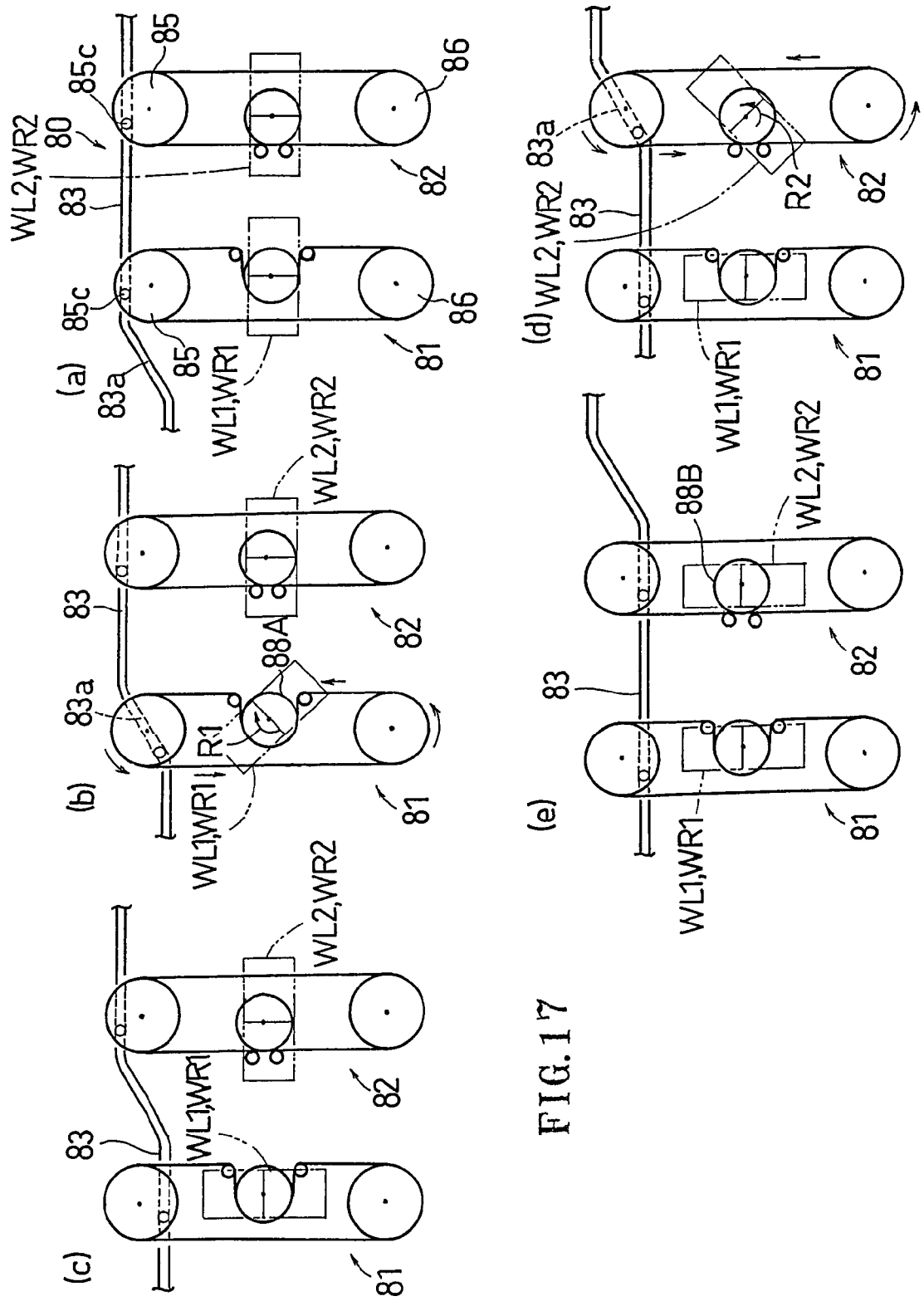
FIG. 17 is a schematic plan view showing an attitude-changing operation.

As shown in FIG. 17(*a*), the drive pulley 85 is provided with a cam follower 85c, whereby as the moving sections 81 and 82 rotate in the circumferential direction of the adjustment drum, the drive pulley 85 rotates in a slant section 83a of the guide groove 83. Along with the rotation of the drive pulley 85, the circumscribed pulley 88A rotates in the first direction R1 as shown in FIGS. 17(*a*) to 17(*c*), and the first pad 89A of FIG. 5 on the pulley 88A turns by 90 degrees in the first direction R1. Thus, the attitude of the first group of panels WL1 to WR1 is changed to an attitude that is obtained by a 90 degrees rotation in the first direction R1.

Along with the rotation of the driven pulley 85, the inscribed pulley 88B rotates in the second direction R2 as shown in FIGS. 17(*c*) to 17(*e*), and the second pad 89B of FIG. 5 on the pulley 88B turns by 90 degrees in the second direction R2. Thus, the attitude of the second group of panels WL2 to WR2 is changed by 90 degrees in the second direction R2.

Another attitude-changing device and method will now be described.

Figure 18:
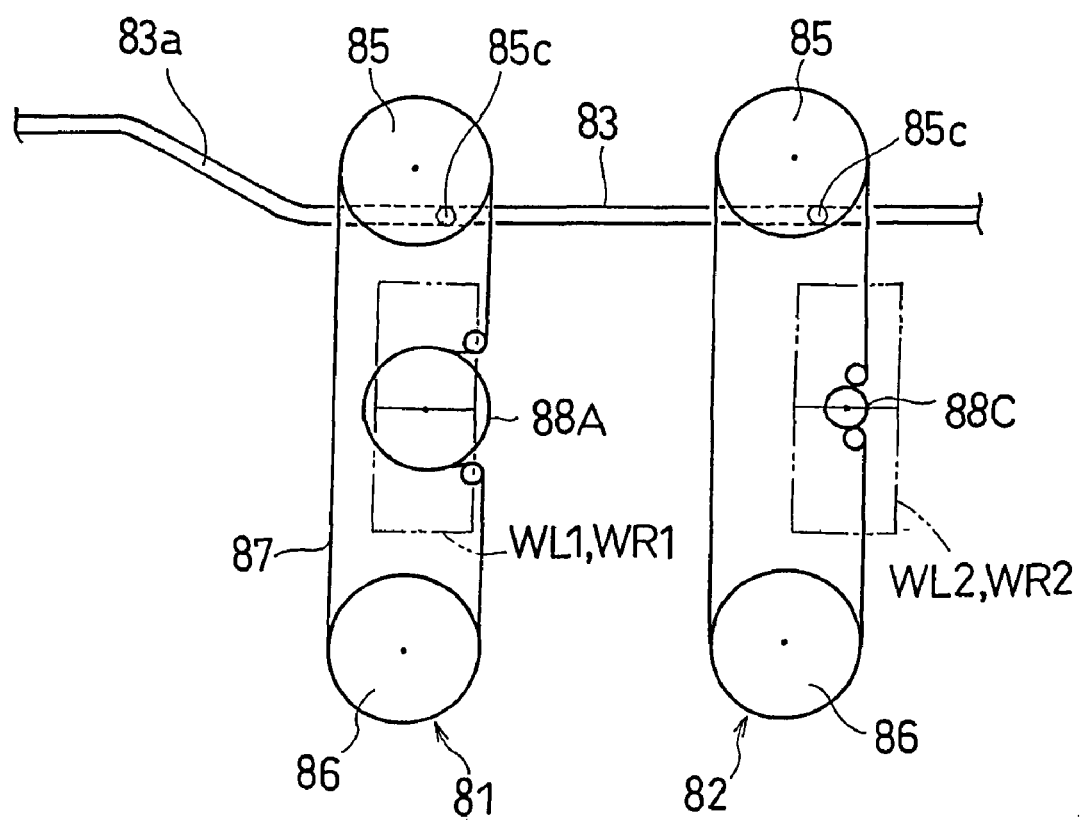
FIG. 18 is a schematic plan view showing another example of an attitude-changing device.

As shown in FIG. 18, the first and second moving sections 81 and 82 include first and second circumscribed pulleys 88A and 88C, respectively. The outer diameter ratio between the first circumscribed pulley 88A and the second circumscribed pulley 88C is set to 3:1. Therefore, in the slant section 83a, the first circumscribed pulley 88A rotates by 90 degrees in the first direction, whereas the inscribed pulley 88B rotates by 270 degrees in the first direction in the same slant section 83a. Thus, two groups of panels WL1-WR1 and WL2-WR2 are rotated so that their attitudes will be the same.

In order to perform the attitude-changing process shown in FIGS. 16 to 18, the core sections need to be spaced apart from each other in advance.

Figure 19:
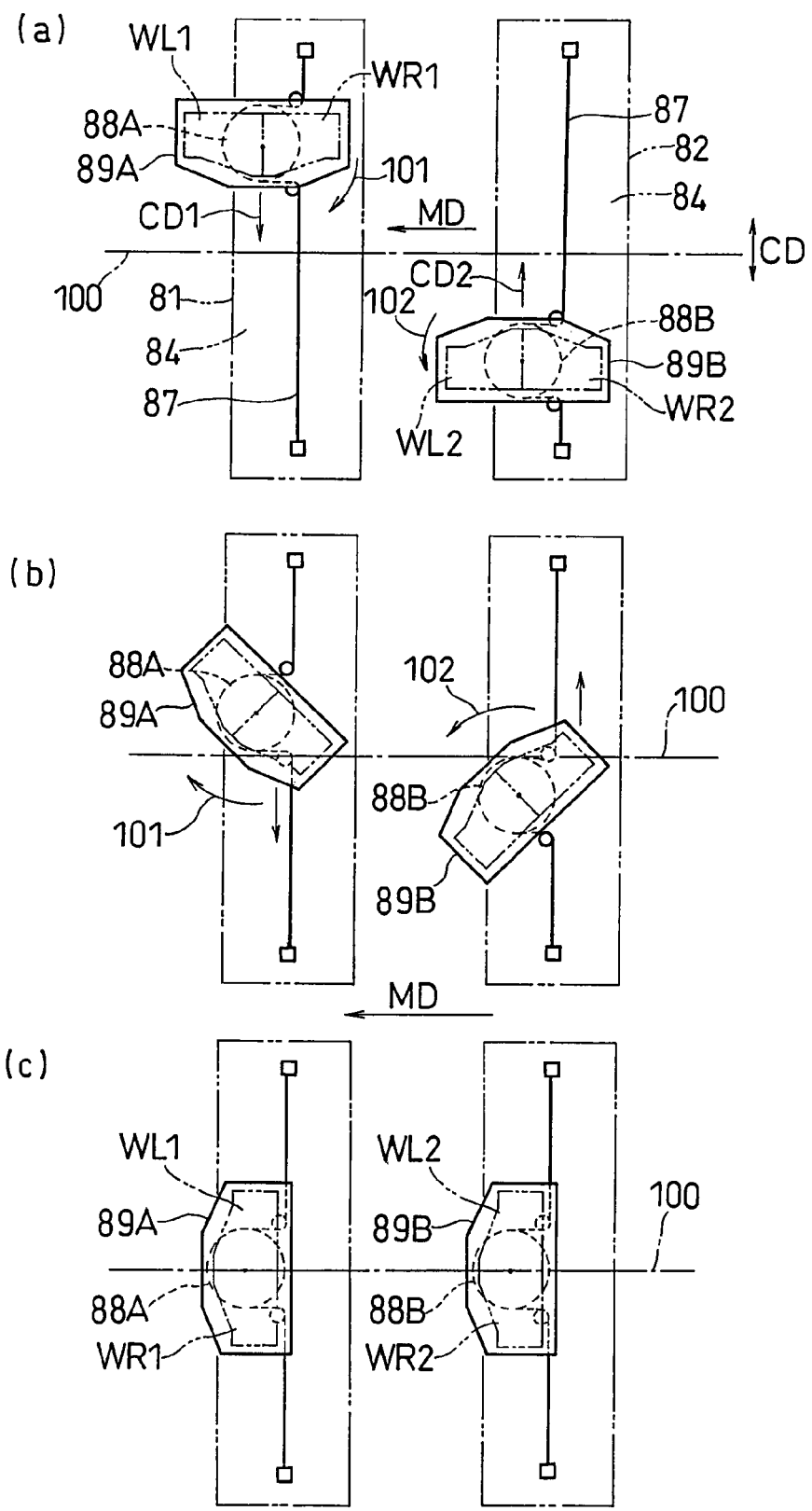
FIGS. 19(a) to 19(c) are schematic plan views each showing still another example of an attitude-changing device.

FIGS. 19(*a*) to 19(*c*) show still another attitude-changing device and method.

In this embodiment, the cut panels are aligned with each other while changing the attitudes thereof, as shown in FIGS. 19(*a*) to 19(*c*). The present embodiment will now be described briefly.

In FIG. 19(*a*), the first and second moving sections 81 and 82 each include the pad base 84. Opposite ends of the timing belt 87 are fixed on the pad base 84. The first and second circumscribed pulleys 88A and 88B are engaged with the timing belt 87. The first pad 89A and the second pad 89B are mounted on the first circumscribed pulley 88A of the first moving section 81 and the second circumscribed pulley 88B of the second moving section 82, respectively.

The circumscribed pulleys 88A and 88B can reciprocate in the width direction CD generally perpendicular to the moving direction MD of the pad base 84, and rotate in the forward direction and in the reverse direction as they reciprocate in the CD direction. Therefore, the first pad 89A on the circumscribed pulley 88A rotates in the first rotation direction 101 as it moves in the first width direction CD1 coming closer to the center line 100, and the second pad 89B on the second circumscribed pulley 88B rotates in the second rotation direction 102 as it moves in the second width direction CD2 coming closer to the center line 100. The first width direction CD1 is a direction opposite to the second width direction CD2, and the first rotation direction 101 is a direction opposite to the second rotation direction 102.

An example of an attitude-changing and alignment method of the present embodiment will now be described.

In the present embodiment, the first cut panels WL1 and WR1 and the second cut panels WL2 and WR2 on the pads 89A and 89B as shown in FIG. 19(*a*) transition from a state where they are spaced apart from each other both in the CD direction and in the MD direction to a state where they are aligned in the flow direction MD as shown in FIG. 19(*c*). Specifically, through the attitude-changing process and the movement in the CD direction, the panels transition from a state where the first cut panels WL1 and WR1 and the second cut panels WL2 and WR2 are apart from each other in the CD direction and are also apart from each other in the MD direction as shown in (*c*) and (*h*) of FIG. 13 to a state where they are aligned with each other as shown in (*m*) of FIG. 13.

This will be described in greater detail. As shown in FIGS. 19(*a*) to 19(*c*), the first pad 89A rotates, together with the circumscribed pulley 88A, by about 90 degrees in the first rotation direction 101, while the first pad 89A is carried in the flow direction MD to move in the first width direction CD1 to the position of the center line 100. The second pad 89B rotates, together with the second circumscribed pulley 88B, by about 90 degrees in the second rotation direction 102, while the second pad 89B is carried in the flow direction MD to move in the second width direction CD2 to the position of the center line 100. Thus, the first cut panels WL1 and WR1 on the pad 89A and the second cut panels WL2 and WR2 on the pad 89B are aligned with each other. The movement of the first pad 89A and the second pad 89B in the width direction CD is guided by a cam mechanism (not shown), or the like.

Fourth Embodiment

Another example of a method for producing the diaper of FIG. 1(*a*) will now be described.

Figure 20:
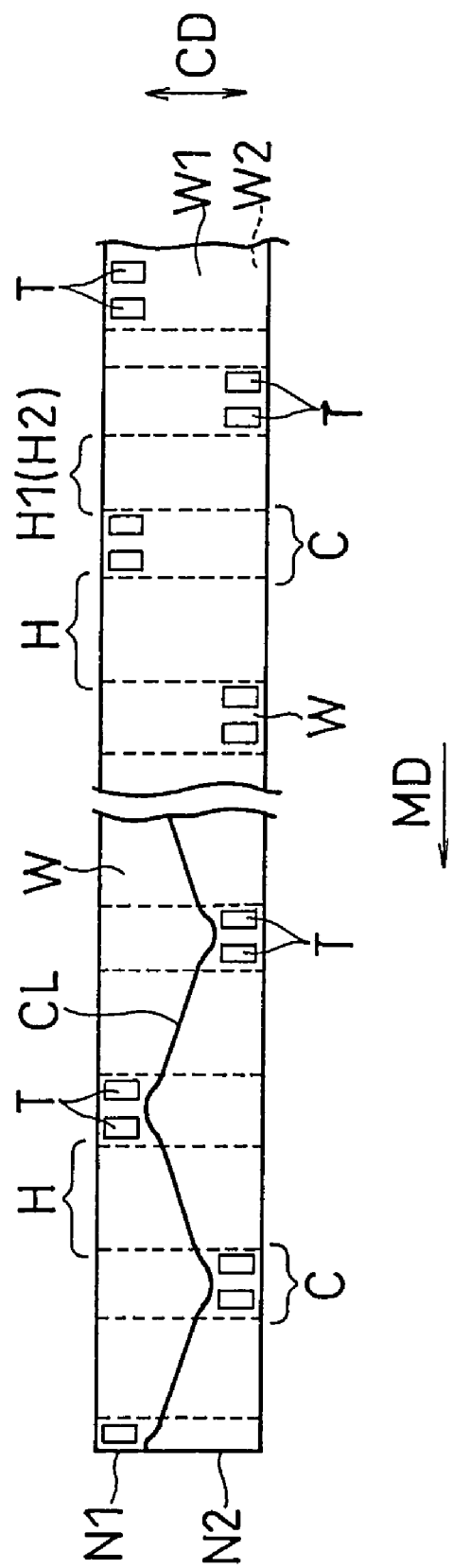
FIG. 20 is a schematic plan view showing a step of slitting a laminate according to the fourth embodiment.

(*a*) of FIG. 20 shows the laminate W. The method for producing the laminate W may be the above-described method for producing the laminate W, and will not be further described below. Other than the above-described production method, the following method may be used, for example. Slack portions may be provided on both of two sheet-like materials, and the elastic member G may be introduced between the two sheet-like materials. In this method, gathers (shirring) can be formed by pulling the portion sandwiched between the slack portions to remove the slack of the slack portions.

In the fourth embodiment, the elastic member G is provided as in the first embodiment, but it is not illustrated in the figure.

As shown of (b) in FIG. 20, the laminate W is cut off along a wave-shaped cut-off line CL while being carried. For example, the cut-off line CL is in a wave shape extending in the flow direction MD and having a predetermined wavelength. By the cutting process, the laminate W is divided into first and second divided laminates N1 and N2 having generally the same shape with their phases being shifted from each other (i.e. the laminates N1 and N2 being out of phase) in the flow direction MD by one half the wavelength.

After the division process, the first and second divided laminates N1 and N2 are spaced apart from each other in the up-down direction Z (the direction perpendicular to the surfaces of the divided laminates N1 and N2) of FIG. 23. After the spacing process, the first divided laminate N1 is carried while being moved slightly toward the center line 100 as shown in (a) of FIG. 21. Thus, the first divided laminate N1 is carried along the center line 100. The first divided laminate N1 is carried while its attitude being in symmetry with that of the second divided laminate N2 shown in (b) of FIG. 21.

Figure 21:
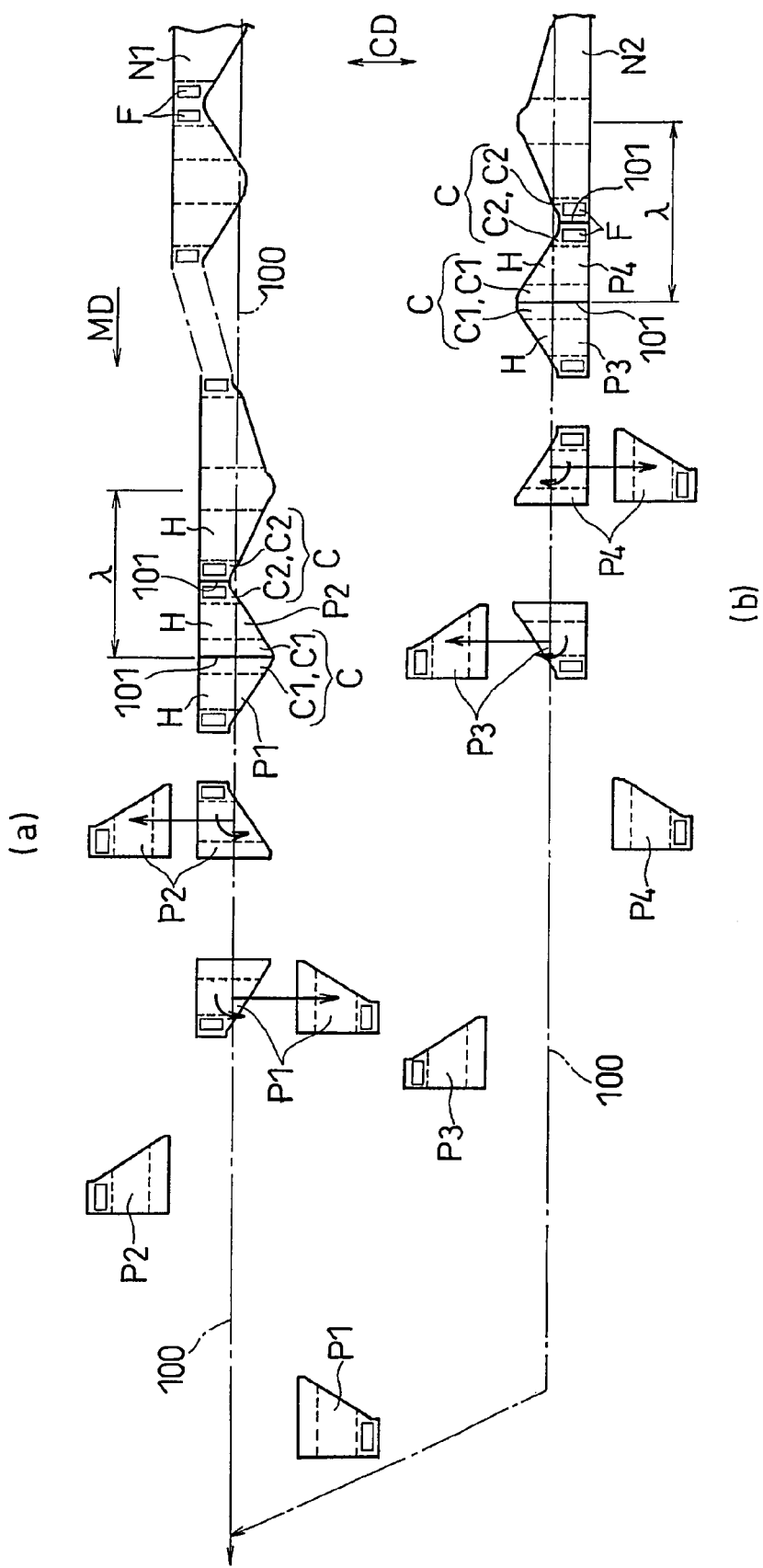
FIG. 21 is a schematic plan view showing a method for producing cut panels of the fourth embodiment, and showing how the cut panels are rotated and moved.

First and Second Cut Panels P1 and P2:

Then, as shown in (a) of FIG. 21, a tip portion of the first divided laminate N1, among the first and second divided laminates N1 and N2, is cut off to a predetermined length along the cut-off line 101 extending in the width direction CD. By repeating the cutting process, there are produced, for every iteration of one wavelength λ(lambda), first and second cut panels P1 and P2 being generally in line symmetry with each other with respect to the cut-off line 101 therebetween.

In the laminate W shown in (a) of FIG. 21, the tension in the flow direction MD has been removed, and the extended elastic member is contracting in the flow direction MD, thereby forming gathers in a contractile portion H. The laminate W of such a contracted state is cut off along the cut-off line 101, thereby producing, from the non-contractile portion C, the bond portions C1 and C1 being wider in the width direction CD, and the fastening portions C2 and C2 on which the touch fastener F is attached.

Therefore, in the first and second cut panels P1 and P2 formed by the cutting process, the contractile portion H of the gathers is produced between the flat bonded portion C1 and the flat fastening portion C2.

After being cut off, the first and second cut panels P1 and P2 are spaced apart from each other in the flow direction MD. The first and second cut panels P1 and P2 are rotated by about 90 degrees in the same direction, whereby the attitudes thereof change, and the distance between the first cut panel P1 and the second cut panel P2 in the width direction CD is increased.

After the rotation process, the cut panels P1 and P2 are spaced apart from each other so that the distance between the first cut panel P1 and the second cut panel P2 in the flow direction MD becomes equal to the length of the main body portion 21 or 22 in the flow direction MD as shown in FIG. 22(a). Then, the bond portions C1 and C1 of the first and second cut panels P1 and P2 are bonded to a sheet-like member (hereinafter referred to as the "main body sheet") CW to be the first and second main body portions 21 and 22.

The main body sheet CW is continuously carried in the flow direction MD. For example, after the bonding of the third and fourth cut panels to be described later, the main body sheet CW is cut along the cut-off line 201 to form the main body portions 21 and 22. By this cutting process, the first main body portion 21 and the second main body portion 22 are produced from the main body sheet CW. Therefore, it can be said that a portion of the main body sheet CW to be the first main body portion 21 and a portion thereof to be the second main body portion 22 are carried alternately.

The first cut panel P1 is bonded to the first side CS1 of a portion of the main body sheet CW to be the first main body portion 21. The second cut panel P2 is bonded to the second side CS2 of a portion of the main body sheet CW to be the second main body portion 22.

Third and Fourth Cut Panels P3 and P4:

As with the first divided laminate N1, a tip portion of the second divided laminate N2 is repeatedly cut off, thus producing, for every iteration of one wavelength λ(lambda), third and fourth cut panels P3 and P4 being generally in line symmetry with each other, as shown in (b) of FIG. 21.

After being cut off, the third and fourth cut panels P3 and P4 are spaced apart from each other in the flow direction MD. The third and fourth cut panels P3 and P4 are rotated by about 90 degrees in the same direction, whereby the attitudes thereof change, and the distance between the third cut panel P3 and the fourth cut panel P4 in the width direction CD is increased.

After the rotation process, the cut panels P3 and P4 are spaced apart from each other so that the distance between the third cut panel P3 and the fourth cut panel P4 in the flow direction MD becomes equal to the length of the main body portion 21 or 22 in the flow direction MD as shown in FIG. 22(b). Then, the bond portions C1 and C1 of the third and fourth cut panels P3 and P4 are bonded to the first and second main body portions 21 and 22, respectively, of the main body sheet CW.

As shown in FIG. 22(b), the first cut panel P1 and the fourth cut panel P4 are aligned with each other in the flow direction MD of the main body sheet CW. The second cut panel P2 and the third cut panel P3 are aligned with each other in the flow direction MD of the main body sheet CW. Therefore, the third and fourth cut panels P3 and P4 are positioned so as to oppose the first and second cut panels P1 and P2, respectively, via the center line 100 therebetween.

The third cut panel P3 is bonded to the second side CS2 of a portion of the main body sheet CW to be the first main body portion 21. The fourth cut panel P4 is bonded to the first side CS1 of a portion of the main body sheet CW to be the second main body portion 22.

Then, the main body sheet CW is cut into a predetermined shape to produce a diaper as shown in FIG. 1(a). Therefore, a diaper in which the first cut panel P1 and the third cut panel P3 are bonded to the first main body portion 21 and a diaper in which the second cut panel P2 and the fourth cut panel P4 are bonded to the second main body portion 22 are produced alternately.

The method for placing the cut panels P1 to P4 may be such that the first cut panel P1 is bonded on one side of the main body sheet CW to be the main body portion 21 (22), and the second or third cut panel P2 or P3 is bonded on a side of the main body sheet CW to be the main body portion that is opposite to the side on which the first cut panel P1 is bonded.

The fourth cut panel P4 may be bonded on either the left side or the right side of the main body sheet CW to be the main body portion 21 (22), and the third or second cut panel P3 or P2 may be bonded on a side of the main body sheet CW to be the main body portion 21 (22) that is opposite to the side on which the fourth cut panel P4 is bonded.

An underpants-type worn article may be formed by bonding the fastening portion C2 of the side panels P1 and P3 (P2 and P4) of FIG. 22(b) to the main body portion 21 (22). In such a case, the touch fastener F does not have to be provided in the fastening portion C2.

Production Device:

An apparatus for producing the diaper of the present invention will now be described.

As shown in FIG. 23, the laminate W, which is produced by the method and the device described above, is introduced into a slitter 220 to be slit, thus producing the first and second divided laminates (an example of the first and second divided sheets) N1 and N2.

After the slitting process, the first divided laminate N1 is carried while being slightly moved by a web guider 219 in the width direction toward the center line 100 ((a) of FIG. 21), so as to be introduced into a first adjustment cutter 231. The second divided laminate N2 is carried above the first divided laminate N1, so as to be introduced into a second adjustment cutter 232.

A tip portion of the first divided laminate N1 is cut by a cutter 230b of the first adjustment cutter 231 along the cut-off line 101 ((a) of FIG. 21). The cut panels P1 and P2 produced by the cutting process are slightly spaced apart in the flow direction MD with respect to the uncut first divided laminate N1.

The first adjustment cutter 231 includes a carrying drum 230a for sucking and carrying a tip portion of the first divided laminate N1, and the cutter 230b. The circumferential velocity V21 of each pad (not shown) provided on the carrying drum 230a is varied periodically. Specifically, each pad of the carrying drum 230a is decelerated after receiving the first divided laminate N1 at the upstream side at the carrying velocity V11 of the first divided laminate N1. With the provision of the deceleration process, the elastic member of a portion to be the gathers of the side panel may contract.

After the tip portion of the first divided laminate N1 is cut by the cutter 230b along the cut-off line 101 ((a) of FIG. 21), the side panels P1 and P2, produced by the cutting process, are carried to the downstream side by the carrying drum 230a. Pads may be accelerated while carrying the side panels P1 and P2 to the downstream side so that the side panel P1 and the next side panel P2 are spaced apart from each other and the side panel P2 and the next side panel P1 are spaced apart from each other in the flow direction MD.

First Interval-Increasing and Rotating Device 241:

The cut panels P1 and P2, produced by the cutting process, are transferred to a first interval-increasing and rotating device 241 downstream.

The first interval-increasing and rotating device 241 is a device for spacing the first and second cut panels P1 and P2 apart from each other while rotating each of them by 90 degrees, as shown in (a) of FIG. 21. The first interval-increasing and rotating device 241 includes a plurality of pads spaced apart from each other. After the pads receive the cut panels P1 and P2 from the first adjustment cutter 231 at the receiving position RP4, the pads moves while sucking and hold the cut panels P1 and P2 thereon, and then hand over the cut panels P1 and P2 to a first interval adjustment device 271 downstream at the hand-over position SP4.

As the pads of the first interval-increasing and rotating device 241 rotate from the receiving position RP4 to the hand-over position SP4, the interval between the pads increases, thus increasing the interval between the cut panels P1 and P2 in the flow direction MD. At the same time, the pads rotate by about 90 degrees in the same direction, thereby changing the attitudes thereof, and move significantly in the width direction CD. Thus, the interval between the first cut panel P1 and the second cut panel P2 is increased, while changing the attitudes of the cut panels P1 and P2 ((a) of FIG. 21).

After the process of increasing the interval between cut panels and changing the attitudes thereof, the interval between the first cut panels P1 and P1 is further increased by the first interval adjustment device 271 downstream. Therefore, the pitch of the first cut panels P1 and P1 of FIG. 22(b) is adjusted to twice the product length Lc. Thus, the positions at which the cut panels are bonded to the main body sheet CW are adjusted and an adhesive is applied by an application device G7. Then, the cut panels P1 and P2 are bonded to the main body sheet CW at predetermined positions (FIG. 22(a)).

The pitch of the second cut panels P2 and P2 of FIG. 22(b) in the flow direction MD is also adjusted to twice the length Lc of the main body portion in the flow direction MD.

The interval adjustment device 271 may be, for example, a drum including a plurality of pads.

As with the first divided laminate N1, the second divided laminate N2 is subjected to the cutting process, the interval adjustment process and the rotation and interval-increasing process shown in (b) of FIG. 21 by the second adjustment cutter 232, a second interval-increasing and rotating device 242 and a second adjustment device 272, after which the third and fourth cut panels P3 and P4 are bonded to the main body sheet CW at predetermined positions as shown in FIG. 22(b). The second adjustment cutter 232, the second interval-increasing and rotating device 242 and the second interval adjustment device 272 have similar functions to those of the first adjustment cutter 231, the first interval-increasing and rotating device 241 and the first interval adjustment device 271 for the production and the adjustment of the third and fourth cut panels P3 and P4.

Thus, with the first and second interval adjustment devices 271 and 272, the cut panels P1 to P4 are placed at predetermined positions of the main body sheet CW to be side panels, thus producing a diaper as shown in FIG. 1(a).

While preferred embodiments of the present invention have been described above with reference to the drawings, obvious variations and modifications will readily occur to those skilled in the art upon reading the present specification.

For example, the shape of a cut panel is not limited to a trapezoidal shape or a wave shape.

The main body portion is only required to include an absorbent core, and is not limited to any particular embodiment with respect to the shape thereof, how different sheets are layered, etc.

Thus, such variations and modifications shall fall within the scope of the present invention as defined by the appended claims.

INDUSTRIAL APPLICABILITY

The present invention is applicable to disposable diapers and underpants.

The invention claimed is:

1. A method for producing a worn article in which a pair of side panels each including two sheet-like materials and elastic threads sandwiched between the two sheet-like materials are attached to a main body portion, the method comprising the steps of:

feeding the elastic threads between a pair of sheet-like materials along a flow direction of the pair of sheet-like materials so as to obtain a laminate to be the side panels, wherein the elastic threads are continuous in the flow direction of the sheet-like materials and shrinks in the flow direction; thereafter cutting the laminate along a predetermined wave-shaped first cut-off line extending in the flow direction and having peaks and troughs alternate with each other to produce first and second divided laminates, which are separated from each other in a width direction of the sheet-like materials; thereafter cutting the first divided laminate along a second cut-off line extending in the width direction in each of the troughs of the wave-shaped first cut-off line and also along a third cut-off line extending in the width direction in each of the peaks of the wave-shaped first cut-off line to obtain a pair of first cut panels adjacent to each other in the third cut-off line;

cutting the second divided laminate along a fourth cut-off line extending in the width direction in each of the troughs of the wave-shaped first cut-off line and also along a fifth cut-off line extending in the width direction in each of the peaks of the wave-shaped first cut-off line to obtain a pair of second cut panels adjacent to each other in the fifth cut-off line;

changing an attitude of the pair of first cut panels to an attitude that is obtained by a rotation of about 90 degrees with respect to the flow direction after the step of obtaining the first cut panels;

changing an attitude of the pair of second cut panels to an attitude that is obtained by a rotation of about 90 degrees with respect to the flow direction after the step of obtaining the second cut panels;

spacing the attitude-changed pair of first cut panels apart from each other in the width direction, which is generally perpendicular to the flow direction, after the step of changing the attitude of the pair of first cut panels;

spacing the attitude-changed pair of second cut panels apart from each other in the width direction, which is generally perpendicular to the flow direction, after the step of changing the attitude of the pair of second cut panels;

attaching the pair of first cut panels whose attitude has been changed and spaced apart from each other to a sheet-like member to be the main body portion, one on a left side and the other on a right side of the sheet-like member after the steps of changing the attitude of the pair of first cut panels and spacing the attitude-changed pair of first cut panels apart from each other;

attaching the pair of second cut panels whose attitude has been changed and spaced apart from each other to the sheet-like member to be the main body portion, one on the left side and the other on the right side of the sheet-like member after the steps of changing the attitude of the pair of second cut panels and spacing the attitude-changed pair of second cut panels apart from each other.

2. A method for producing a worn article in which a pair of side panels are attached to a left side and a right side of a main body portion, the method comprising the steps of:

cutting a continuous sheet-like laminate, the laminate comprising elastic threads along a flow direction of the laminate between a pair of sheet-like materials, which is being carried, along a first cut-off line extending in the flow direction to form first and second divided laminates, the first cut-off line having a wave shape of a predetermined wavelength and having peaks and troughs alternate with each other; thereafter cutting the first divided laminate at a predetermined interval in the flow direction along a second cut-off line extending in a width direction of the laminate perpendicular to the flow direction in each of the peaks of the wave-shaped fist cut-off line and also along a third cut-off line extending in the width direction in each of the troughs of the wave-shaped first cut-off line to produce, for every iteration of the wavelength, a first cut panel and a second cut panel being generally in line symmetry with each other;

cutting the second divided laminate at a predetermined interval in the flow direction along a fourth cut-off line extending in the width direction in each of the peaks of the wave-shaped fist cut-off line and also along a fifth cut-off line extending in the width direction in each of the troughs of the wave-shaped first cut-off line to produce, for every iteration of the wavelength, a third cut panel and a fourth cut panel being generally in line symmetry with each other;

spacing the first cut panel and the second cut panel apart from each other in the flow direction after the step of producing the first and second cut panels;

spacing the third cut panel and the fourth cut panel apart from each other in the flow direction after the step of producing the third and fourth cut panels;

changing an attitude of each of the first and second cut panels to an attitude that is obtained by a rotation of about 90 degrees with respect to the flow direction after the step of spacing the first and second cut panels apart from each other;

changing an attitude of each of the third and fourth cut panels to an attitude that is obtained by a rotation of about 90 degrees with respect to the flow direction after the step of spacing the third and fourth cut panels apart from each other;

increasing a distance between the first cut panel and the second cut panel in a width direction of the laminate, which is generally perpendicular to the flow direction after the step of changing the attitude of the first and second cut panels;

increasing a distance between the third cut panel and the fourth cut panel in the width direction of the laminate after the step of changing the attitude of the third and fourth cut panels;

attaching the first cut panel on a left side and the second or third cut panel on a right side of a sheet-like member to be the main body portion, and attaching the fourth cut panel on the left side and the third or second cut panel on the right side of the sheet-like member to be the main body portion after the steps of increasing the distance between the first and second cut panels and increasing the distance between the third and fourth cut panels.

3. A method for producing a worn article according to claim 2, further comprising a step of aligning the first cut panel and the fourth cut panel with each other in the flow direction while aligning the second cut panel and the third cut panel with each other in the flow direction.

4. A method for producing a worn article according to claim 2, wherein in the step of cutting the continuous sheet-like laminate to form the first and second divided laminates, the divided laminates are formed with a phase of the first divided laminate being shifted from that of the second divided laminate in the flow direction by one half of the wavelength.

5. A method for producing a worn article according to claim 1, wherein each of the first and second cut panels forms a side panel without being trimmed.

6. A method for producing a worn article according to claim 1, further comprising a step of attaching a fastening element to the laminate, the fastening element being used for fastening the side panels to the main body portion when the worn article is worn, wherein in the step of cutting the laminate to obtain the cut panels, the fastening element, together with the laminate, is cut into two pieces so that each cut panel includes at least a cut-off fastening element.

7. A method for producing a worn article according to claim 1, wherein the elastic threads exert a contractile force on the laminate in a contractile portion, and wherein non-contractile portions extending in a direction perpendicular to the flow direction and having no contractile force exerted thereon are formed in the laminate at a predetermined interval in the flow direction, and, in the step of cutting the laminate to obtain the cut panels, the laminate is cut along each non-contractile portion so that each of the cut panels includes at least a part of the non-contractile portion, and in the step of attaching the pair of cut panels to the sheet-like member to be the main body portion, a part of the non-contractile portions of the cut panels is attached to the sheet-like member.

8. A method for producing a worn article according to claim 1, wherein in the step of feeding the elastic threads to obtain the laminate to be the side panels, the elastic threads are fed between the pair of sheet-like materials while the elastic threads are being extended in the flow direction to produce the laminate, and after producing the laminate, the elastic threads of the laminate or the cut panels are relaxed so as to form gathers in the laminate or the cut panels.

* * * * *